US011773155B2

(12) United States Patent
Liu et al.

(10) Patent No.: US 11,773,155 B2
(45) Date of Patent: Oct. 3, 2023

(54) BISPECIFIC ANTIBODY AGAINST RABIES VIRUS, AND APPLICATION THEREOF

(71) Applicants: Beijing Wisdomab Biotechnology Co., Ltd, Beijing (CN); GENRIX (Shanghai) Biopharmaceutical Co. Ltd., Shanghai (CN); Chongqing GENRIX Biopharmaceutical Co., Ltd., Chongqing (CN)

(72) Inventors: Zhigang Liu, Beijing (CN); Xiaobo Hao, Beijing (CN); Yulan Liu, Beijing (CN); Jingjing Guo, Beijing (CN)

(73) Assignees: Beijing Wisdomab Biotechnology Co., ltd, Beijing (CN); GENRIX (Shanghai) Biopharmaceutical Co., Ltd., Shanghai (CN); Chongqing GENRIX Biopharmaceutical Co., Ltd., Chongqing (CN)

( * ) Notice: Subject to any disclaimer, the term of this patent is extended or adjusted under 35 U.S.C. 154(b) by 364 days.

(21) Appl. No.: 17/057,100

(22) PCT Filed: Aug. 1, 2019

(86) PCT No.: PCT/CN2019/098836
§ 371 (c)(1),
(2) Date: Nov. 19, 2020

(87) PCT Pub. No.: WO2020/029860
PCT Pub. Date: Feb. 13, 2020

(65) Prior Publication Data

US 2021/0340224 A1 Nov. 4, 2021

(30) Foreign Application Priority Data

Aug. 9, 2018 (CN) ......................... 201810901518.0

(51) Int. Cl.

| | |
|---|---|
| *C07K 16/10* | (2006.01) |
| *A61P 31/14* | (2006.01) |
| *C07K 16/46* | (2006.01) |

(52) U.S. Cl.
CPC .............. *C07K 16/10* (2013.01); *A61P 31/14* (2018.01); *C07K 16/468* (2013.01); *C07K 2317/31* (2013.01); *C07K 2317/33* (2013.01); *C07K 2317/55* (2013.01); *C07K 2317/565* (2013.01); *C07K 2317/622* (2013.01); *C07K 2317/76* (2013.01)

(58) Field of Classification Search
CPC ........................... C07K 16/10; C07K 2317/31; C07K 2317/33; C07K 2317/55; C07K 2317/565; C07K 2317/622; C07K 2317/76; C07K 16/468; A61P 31/14; A61K 2039/505
See application file for complete search history.

(56) References Cited

U.S. PATENT DOCUMENTS

| | | | |
|---|---|---|---|
| 4,816,567 A | 3/1989 | Cabilly et al. | |
| 7,579,446 B2 | 8/2009 | Bakker et al. | |
| 7,740,850 B2 | 6/2010 | Zhu et al. | |
| 7,740,852 B2 | 6/2010 | Holland | |
| 7,919,257 B2 | 4/2011 | Hoogenboom et al. | |
| 9,005,624 B2 * | 4/2015 | Bakker | G01N 33/56983 424/159.1 |
| 9,193,780 B2 | 11/2015 | Hultberg et al. | |
| 9,834,595 B2 * | 12/2017 | Storteles | A61P 31/14 |
| 2008/0226652 A1 | 9/2008 | Bakker et al. | |
| 2016/0120799 A1 | 5/2016 | Chiang et al. | |
| 2019/0022211 A1 | 1/2019 | Chang et al. | |
| 2020/0131251 A1 | 4/2020 | Mhalasakant et al. | |

FOREIGN PATENT DOCUMENTS

| | | |
|---|---|---|
| CN | 1961002 A | 5/2007 |
| CN | 102112155 A | 6/2011 |
| CN | 102139106 A | 8/2011 |
| CN | 107709360 | 2/2018 |
| CN | 110317267 A | 10/2019 |
| WO | WO 2004/106375 A1 | 12/2004 |
| WO | WO 2009/147248 A2 | 12/2009 |
| WO | WO 2018/116198 A1 | 6/2018 |

OTHER PUBLICATIONS

Chabaud-Riou et al., G-protein based ELISA as a potency test for rabies vaccines, Biologicals 2017, 6 pages.
Wang et al., Preparation and identification of monoclonal antibody specific to the V region of rabies virus G protein, Chinese Veterinary Science, 2017, 47(05), pages 592-596.
Chinese Patent Application No. 2020102288659, First Office Action dated Jun. 15, 2021.
International Patent Application No. PCT/CN2019/098836; International Search Report and Written Opinion dated Nov. 6, 2019; 19 pgs.
Al-Lazikani et al., J. Mol. Biol. 273:927-948 (1997).
Martin et al., Proc. Natl. Acad. Sci.USA86:9268-9272 (1989).
Morrison et al., Proc. Natl. Acad. Sci. USA 81:6851-6855 (1984).
Bakker, A. B. et al. Novel human monoclonal antibody combination effectively neutralizing natural rabies virus variants and individual in vitro escape mutants. J. Virol. 79, 9062-9068.
Marissen et al., Novel rabies virus-neutralizing epitope recognized by human monoclonal antibody: fine mapping and escape mutant analysis, Journal of Virology, Apr. 2005, p. 4672-4678.
Sief et al., Rabies virulence: effect on pathogenicity and sequence characterization of rabies virus mutations affecting antigenic site III of the glycoprotein, Journal of Virology, Mar. 1985, p. 926-934.
Xi et al., Engineering of a novel zipFv using leucine zipper motif against rabies virus glycoprotein G with improved protection potency in vivo, Immunology Letters 186 (2017) 9-14.

(Continued)

*Primary Examiner* — Nicole Kinsey White
*Assistant Examiner* — Ruixue Wang
(74) *Attorney, Agent, or Firm* — Cozen O'Connor

(57) ABSTRACT

The present application provides a bispecific antibody against rabies virus, and an application thereof. The bispecific antibody comprises two antigen-binding fragments binding to different epitopes of G protein of rabies virus, and has rabies virus neutralization activity.

9 Claims, 7 Drawing Sheets

Specification includes a Sequence Listing.

(56) References Cited

OTHER PUBLICATIONS

Yiru et al., Generation and characterization of a human neutralizing bivalent antibody Fab094-DDD against rabies virus, ACTA Universitatis Medicinalis Nanjing (Natural Science), vol. 36, No. 6.
Filippovich et al. Biochemical foundations of human life, 2005, 4 pages.
Hlavacek et al., Steric Effects on Multivalent Ligand-Receptor Binding: Exclusion of Ligand Sites by Bound Cell Surface Receptors, Biophysical Journal vol. 76, Jun. 1999, pp. 3031-3043.
Roitt et al., Immunology fifth edition, 2000, 3 pages.
Yarilin, Fundamentals of Immunology, 1999, 4 pages.
Russian Patent Application No. 2020130632/10(055540), English Translation of Office Action dated Aug. 4, 2021, 4 pages.
Russian Patent Application No. 2020130632/10(055540), Office Action dated Aug. 4, 2021, 5 pages.
Russian Patent Application No. 2020130632/10(055540), Search Report dated Aug. 4, 2021, 2 pages.

\* cited by examiner

BISPECIFIC ANTIBODY AGAINST RABIES VIRUS, AND APPLICATION THEREOF

CROSS REFERENCE TO RELATED APPLICATION

The present application is a 35 U.S.C. § 371 filing of International Application No. PCT/CN2019/098836 filed Aug. 1, 2019, which claims priority to Chinese Patent Application No. 201810901518.0 filed on Aug. 9, 2018, which is incorporated herein by reference in its entirety.

TECHNICAL FIELD

The present application generally relates to the field of genetic engineering and antibody drugs. In particular, the present application relates to bispecific antibodies against rabies virus and use thereof.

BACKGROUND

Rabies is an acute infectious disease caused by rabies virus, and affects both humans and animals. Rabies virus is transmitted mainly among dogs, wolves, and cats, but other mammals such as raccoons, skunks, bats, and foxes are also common hosts. Animals transmit the virus by biting each other, and humans are frequently infected by bites of diseased animals. Currently, there is no effective treatment for rabies. The mortality of rabies patients is nearly 100%. Patients generally die from respiratory or circulatory failure within 3-6 days. It is estimated that more than 70,000 people worldwide die each year from the disease and millions need post-exposure treatment.

Rabies virus is a bullet-shaped, enveloped, single-stranded RNA virus, and belongs to the Rhabdoviridae family, and the lyssavirus genus. The genome of rabies virus encodes five viral proteins, i.e. RNA-dependent RNA polymerase (L), nucleoprotein (N), phosphorylated protein (P), matrix protein (M) located inside the envelope of the viral protein, and outer surface glycoprotein (G). The glycoprotein (G protein) of rabies virus binds to acetylcholine, which determines the neurophagocytosis of rabies virus. The G protein (62-67 kDa) is a type I glycoprotein consisting of 505 amino acids, forms a protuberance covering the outer surface of the viral particle envelope, and has been shown to induce viral neutralizing antibodies. The G protein has at least five neutralizing epitopes. Epitope II is a discontinuous spatial epitope including amino acid residues 34-42 and amino acid residues 198-200. Epitope III is located at positions 330-338 and is a linear epitope. About 97% of the reported antibodies recognize epitope II and epitope III. Rabies virus neutralizing antibody CR4098 binds to epitope III. Few antibodies recognize epitope I and epitope IV. Rabies virus neutralizing antibody CR57 recognizes linear epitope I, i.e., position 218-240, in which the core binding domain is KLCGVL at position 226-231. Epitope IV contains residues 251 and 264. Yet another epitope is microepitope a that does not overlap with epitope III and separate from epitope III by three amino acid residues, and has only two amino acid residues 342-343.

For prevention and treatment of rabies virus, WHO recommends that, for class III exposure and exposure above class II with wildlife bites, the subjects should receive both active and passive immunotherapies for rapid protection. Currently, the development of rabies virus vaccines for active treatment is relatively mature, and multiple rabies virus vaccines are marketed domestically and abroad for active prevention of rabies virus. While the drugs used for passive treatment after rabies virus exposure are mainly human rabies immune globulin (HRIG) and equine rabies immune globulin (ERIG). Since ERIG is a heterologous protein to humans, it sometimes comes up with serious side effects. HRIG is expensive, has limited supply and has risk of potential contamination by blood-borne pathogens. There is a clinical need to develop novel passive therapeutic drugs for rabies virus infection.

In 1989, Schumacherl et al. prepared a number of murine monoclonal antibodies against the glycoprotein and nucleoprotein of rabies virus. The protective experiments against mice and hamsters using such a monoclonal antibody cocktail therapy showed that the method not only had the ability to completely resist the attack of the lethal dose of rabies virus after passive immunization, but also had the post-exposure protective effect. In 1990, Bernhard Dietzschold et al. prepared a number of human anti-rabies virus monoclonal antibodies using cell fusion techniques in which Mab57 showed high affinity to the glycoprotein of rabies virus, widely neutralized rabies virus and provided protection to against mice from rabies virus attack. After obtaining the gene of anti-rabies virus antibodies, it becomes possible to prepare a human anti-rabies virus monoclonal antibodies using a bioreactor. In 2005, Goudsmit et al. and Bakker's research group reported two human monoclonal antibodies CR57 and CR4098 against the G protein of rabies virus. These two monoclonal antibodies were directly mixed in use and compared with HRIG. The result showed that the monoclonal antibody mixture was comparable to HRIG in post-exposure prophylaxis and had good cross-reactivity with multiple rabies virus strains, demonstrating the practical availability of recombinant human anti-rabies virus monoclonal antibodies, or even replacement of RIG. Currently, drug CL184 based on the two monoclonal antibodies has been in clinical research and has not found any side effects at the time of clinical trials. The drug is safe and effective, and may clinically replace RIG for post-exposure prophylaxis. However, CL184, which is being studied clinically, is a mixed preparation based on two monoclonal antibodies and requires relatively high cost for preparation.

The development and use of novel bispecific antibodies against the G protein of rabies virus is desirable in the art.

SUMMARY OF THE INVENTION

In a first aspect, there is provided in the present application a bispecific antibody comprising two antigen-binding fragments that bind to different epitopes of rabies virus G protein, and the bispecific antibody has the activity of neutralizing rabies virus.

In some embodiments, one antigen-binding fragment in the bispecific antibody binds to epitope I of rabies virus G protein and the other antigen-binding fragment binds to epitope III of rabies virus G protein.

In some embodiments, the antigen-binding fragment that binds to epitope I of rabies virus G protein comprises:

HCDR1 having the amino acid sequence of RYTIN, HCDR2 having the amino acid sequence of GIIPIFGTAN-YAQRFQG, HCDR3 having the amino acid sequence of ENLDNSGTYYYFSGWFDP, LCDR1 having the amino acid sequence of TGTSSDIGAYDYVS, LCDR2 having the amino acid sequence of DATKRPS, and LCDR3 having the amino acid sequence of CSYAGDYTPGVV; or HCDR1 having the amino acid sequence of RYSIN, HCDR2 having the amino acid sequence of GIIPIFGTAN-YAQRFQG, HCDR3 having the amino acid sequence of ENLDNSGTYYYYFSGWFDP, LCDR1 having the amino acid sequence of TGTSSDIDGYDFVS, LCDR2 having the amino acid sequence of DATKRPS, and LCDR3 having the amino acid sequence of CSYAGDYTPGVV; or HCDR1 having the amino acid sequence of GYTIN, HCDR2 having the amino acid sequence of GIIPIFGTANYAQRFQG, HCDR3 having the amino acid sequence of ENLDNSGTYYYYFSGWFDP, LCDR1 having the amino acid sequence of TGTSSDLGGYDFVS, LCDR2 having the amino acid sequence of DATKRPS, and LCDR3 having the amino acid sequence of CSYAGDYTPGVV;

wherein the HCDR and LCDR amino acid sequences are defined according to Kabat.

In some embodiments, the antigen-binding fragment that binds to epitope III of rabies virus G protein comprises:

HCDR1 having the amino acid sequence of SYGMH, HCDR2 having the amino acid sequence of TISYDGSIKDYADSVKG, HCDR3 having the amino acid sequence of GDRTGNLDY, LCDR1 having the amino acid sequence of RASQNIRNALN, LCDR2 having the amino acid sequence of DASTRQS, and LCDR3 having the amino acid sequence of QQNSEFPPT;

wherein the HCDR and LCDR amino acid sequences are defined according to Kabat.

In some embodiments, the amino acid sequence of the heavy chain variable region of the antigen-binding fragment that binds to epitope I of rabies virus G protein is as set forth in SEQ ID NO: 24, and the amino acid sequence of the light chain variable region is as set forth in SEQ ID NO: 25; or the amino acid sequence of the heavy chain variable region of the antigen-binding fragment that binds to epitope I of rabies virus G protein is as shown in SEQ ID NO: 26, and the amino acid sequence of the light chain variable region is as shown in SEQ ID NO: 27; or the amino acid sequence of the heavy chain variable region of the antigen-binding fragment that binds to epitope I of rabies virus G protein is shown in SEQ ID NO: 28, and the amino acid sequence of the light chain variable region is shown in SEQ ID NO: 29.

In some embodiments, the amino acid sequence of the heavy chain variable region of the antigen-binding fragment that binds to epitope III of rabies virus G protein is as set forth in SEQ ID NO: 1 and the amino acid sequence of the light chain variable region is as set forth in SEQ ID NO: 3.

In some embodiments, the amino acid sequence of the heavy chain variable region of the antigen-binding fragment that binds to epitope I of rabies virus G protein is as set forth in SEQ ID NO: 24, and the amino acid sequence of the light chain variable region is as set forth in SEQ ID NO: 25; and the amino acid sequence of the heavy chain variable region of the antigen-binding fragment that binds to epitope III of rabies virus G protein is as set forth in SEQ ID NO: 1, and the amino acid sequence of the light chain variable region is as shown in SEQ ID NO: 3; or the amino acid sequence of the heavy chain variable region of the antigen-binding fragment that binds to epitope I of rabies virus G protein is shown in SEQ ID NO: 26, and the amino acid sequence of the light chain variable region is shown in SEQ ID NO: 27; and the amino acid sequence of the heavy chain variable region of the antigen-binding fragment that binds to epitope III of rabies virus G protein is shown in SEQ ID NO: 1, and the amino acid sequence of the light chain variable region is as shown in SEQ ID NO: 3; or the amino acid sequence of the heavy chain variable region of the antigen-binding fragment that binds to epitope I of rabies virus G protein is shown in SEQ ID NO: 28, and the amino acid sequence of the light chain variable region is shown in SEQ ID NO: 29; and the amino acid sequence of the heavy chain variable region of the antigen-binding fragment that binds to epitope III of rabies virus G protein is shown in SEQ ID NO: 1, and the amino acid sequence of the light chain variable region is shown in SEQ ID NO: 3.

In some embodiments, the forms of the two antigen-binding fragments are independently selected from a single chain antibody (scFv) or a Fab fragment.

In some embodiments, the antigen-binding fragment that binds to epitope I of rabies virus G protein is a single chain antibody (scFv) and the antigen-binding fragment that binds to epitope III of rabies virus G protein is a Fab fragment. In some embodiments, the bispecific antibody comprises the amino acid sequence set forth in one of SEQ ID NOS: 32, 33, and 34. In some embodiments, the bispecific antibody comprises the amino acid sequences set forth in SEQ ID NO: 30 and SEQ ID NO: 31.

In a second aspect, there is provided in the present application a pharmaceutical composition comprising a bispecific antibody of the first aspect and a pharmaceutically acceptable excipient, diluent or carrier.

In some embodiments, the pharmaceutical composition is used to prevent or treat rabies.

In a third aspect, there is provided in the present application use of a bispecific antibody of the first aspect in the manufacture of a medicament for prevention or treatment of rabies.

In a fourth aspect, there is provided in the present application a method of preventing or treating rabies, comprising administering to a subject in need thereof abispecific antibody of the first aspect or a pharmaceutical composition of the second aspect.

BRIEF DESCRIPTION OF THE DRAWINGS

FIG. 12A-12C show the ELISA assay result of binding capacity of anti-rabies virus G protein antibodies C34m and S2E3-scFv-Fc to G protein mutants of rabies virus strain CVS-11. FIG. 12A shows the ELISA assay result of binding capacity of C34m and S2E3-scFv-Fc to the fusion protein GCVS11-CD-His. FIG. 12b shows the ELISA assay result of binding capacity of C34m and S2E3-scFv-Fc to the fusion protein GCVS11-G229E-CCD-His. FIG. 12C shows the ELISA assay result of binding capacity of C34m and S2E3-scFv-Fc to the fusion protein GCVS 11-I338T-CCD-His.

Sequence Description

Figure 1:
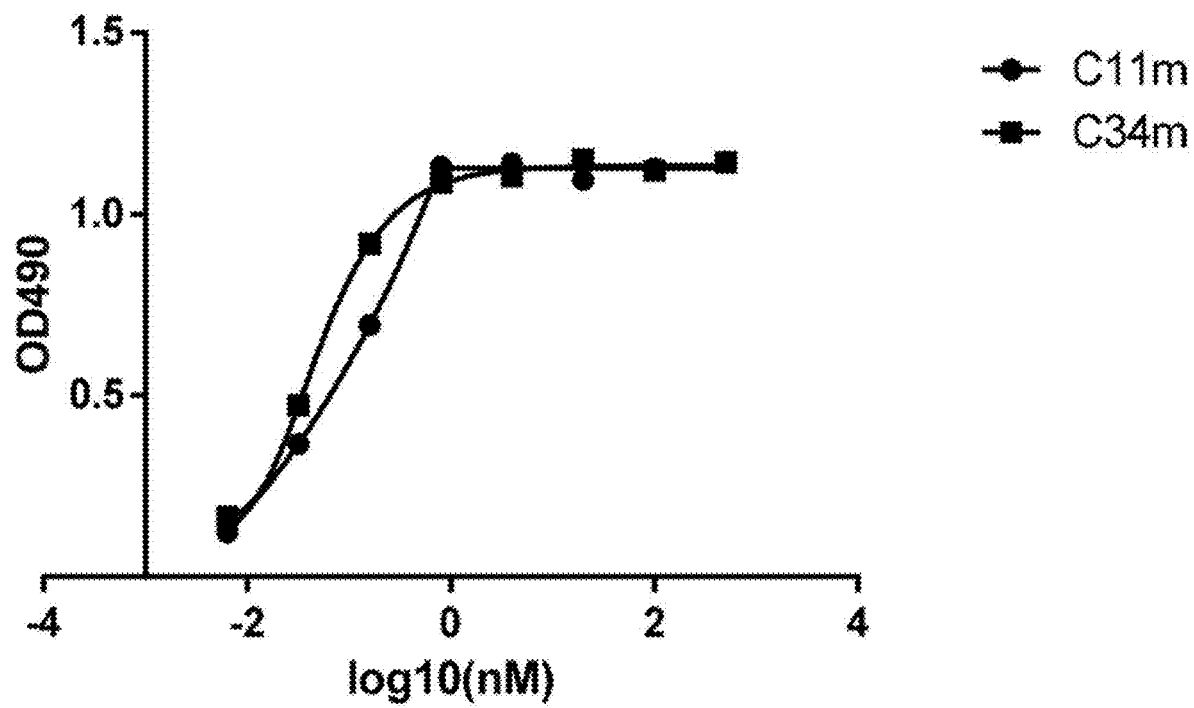
FIG. 1 shows the ELISA assay result of binding capacity of fully human monoclonal antibodies C34m and C11m to inactivated rabies virus.

SEQ ID NO: 1 shows the amino acid sequence of the heavy chain variable region C34mVH of antibody C34m.

SEQ ID NO: 2 shows the amino acid sequence of the heavy chain variable region C11mVH of antibody C11m.

SEQ ID NO: 3 shows the amino acid sequence of the light chain variable region C34mVK of antibody C34m.

SEQ ID NO: 4 shows the amino acid sequence of the light chain variable region C11mVL of antibody C11m.

SEQ ID NO: 5 shows the amino acid sequence of human (*Homo sapiens*) heavy chain constant region CH-IgG1.

SEQ ID NO: 6 shows the amino acid sequence of human (*Homo sapiens*) light chain constant region CK.

SEQ ID NO: 7 shows the amino acid sequence of human (*Homo sapiens*) light chain constant region CL.

SEQ ID NO: 8 shows the amino acid sequence of the single chain antibody C34m-scFv.

SEQ ID NO: 9 shows the amino acid sequence of the single chain antibody C11m-scFv.

SEQ ID NO: 10 shows the amino acid sequence of the Fc segment of human (*Homo sapiens*) IgG1.

SEQ ID NO: 11 shows the amino acid sequence of the Fc segment of murine (*Mus musculus*) IgG2a.

SEQ ID NO: 12 and SEQ ID NO: 15 show the amino acid sequences of the heavy chain variable region CR57VH and light chain variable region CR57VL amino acid sequences of monoclonal antibody CR57 against epitope I of rabies virus G protein, respectively.

SEQ ID NO: 13 and SEQ ID NO: 16 show the amino acid sequences of the heavy chain variable region CR4098VH and light chain variable region CR4098VK of the monoclonal antibody CR4098 against epitope III of rabies virus G protein, respectively.

SEQ ID NO: 14 shows the amino acid sequence of the heavy chain constant region of murine (*Mus musculus*) IgG2a.

SEQ ID NO: 17 shows the amino acid sequence of murine (*Mus musculus*) light chain constant region mCL.

SEQ ID NO: 18 shows the amino acid sequence of murine (*Mus musculus*) light chain constant region mCK.

SEQ ID NO: 19 shows the amino acid sequence of the Fc segment containing the Knob mutation (FcK).

SEQ ID NO: 20 shows the amino acid sequence of the Fc segment containing the Hole mutation (FcH).

SEQ ID NO: 21 shows the amino acid sequence of mutant S1C10-scFv of single chain antibody C11m-scFv.

SEQ ID NO: 22 shows the amino acid sequence of mutant S2A1-scFv of single chain antibody C11m-scFv.

SEQ ID NO: 23 shows the amino acid sequence of mutant S2E3-scFv of single chain antibody C11m-scFv.

SEQ ID NO: 24 and 25 show the amino acid sequences of the heavy chain variable region and light chain variable region of mutant S1C10-scFv of single chain antibody C11m-scFv, respectively.

SEQ ID NOs: 26 and 27 show the amino acid sequences of the heavy chain variable region and the light chain variable region of mutant S2A1-scFv of single chain antibody C11m-scFv, respectively.

SEQ ID NO: 28 and 29 show the amino acid sequences of the heavy chain variable region and light chain variable region of mutant S2E3-scFv of single chain antibody C11m-scFv, respectively.

SEQ ID NO: 30 shows the amino acid sequence of C34mVK-CK.

SEQ ID NO: 31 shows the amino acid sequence of C34mVH-IgG1K.

SEQ ID NO: 32 shows the amino acid sequence of the single chain antibody-Fc fusion protein S2E3-scFv-FcH.

SEQ ID NO: 33 shows the amino acid sequence of the single chain antibody-Fc fusion protein S1C10-scFv-FcH.

SEQ ID NO: 34 shows the amino acid sequence of the single chain antibody-Fc fusion protein S2A1-scFv-FcH.

SEQ ID NO: 35 shows the amino acid sequence of G protein (GCVS11) of wild-type rabies virus strain CVS-11.

SEQ ID NO: 36 shows the amino acid sequence of an epitope I mutant (GCVS11-G229E) of G protein (GCVS11) of rabies virus strain CVS-11.

SEQ ID NO: 37 shows the amino acid sequence of an epitope III mutant (GCVS11-I338T) of G protein (GCVS11) of rabies virus strain CVS-11.

SEQ ID NO: 38 shows the amino acid sequence of the trimeric domain CCD of human (*Homo sapiens*) coronaprotein 1A.

SEQ ID NO: 39 shows the amino acid sequence of the fusion protein GCVS11-CCD-His.

SEQ ID NO: 40 shows the amino acid sequence of the fusion protein GCVS11-G229E-CCD-His.

SEQ ID NO: 41 shows the amino acid sequence of the fusion protein GCVS11-I338T-CCD-His.

DETAILED DESCRIPTION OF THE INVENTION

The inventors of the present application developed novel bispecific antibodies against rabies virus via antibody engineering techniques. In various aspects of the present application, there are provided novel bispecific antibodies against rabies virus, polynucleotides encoding the bispecific antibodies, vectors comprising the polynucleotides, host cells comprising the polynucleotides or vectors, methods of preparing and purifying the bispecific antibodies, and medical and biological use of the bispecific antibodies. According to the sequences of the variable regions of the bispecific antibodies provided herein, full-length bispecific antibody molecules can be constructed for clinical use as a medicament for preventing or treating rabies.

Unless otherwise indicated, the inventions can be practiced using conventional molecular biology, microbiology, cell biology, biochemistry, and immunological techniques in the art.

Unless otherwise indicated, the terms used in the present application have the meanings commonly understood by those skilled in the art.

Definitions

As used herein, the term "antibody" refers to an immunoglobulin molecule that is capable of specifically binding to a target via at least one antigen recognition site located in a variable region of the immunoglobulin molecule. Targets include, but are not limited to, carbohydrates, polynucleotides, lipids, and polypeptides. As used herein, an "antibody" includes not only an intact (i.e., full-length) antibody, but also an antigen-binding fragment thereof (e.g., Fab, Fab', F(ab)$_2$, Fv), a variant thereof, a fusion protein comprising portions of an antibody, a humanized antibody, a chimeric antibody, a diabody, a linear antibody, a single-chain antibody, a multi-specific antibody (e.g., a bispecific antibody), and any other modified formats of an immunoglobulin molecule comprising a desired specific antigen recognition site, including a glycosylated variant of an antibody, an amino acid sequence variant of an antibody, and a covalently modified antibody.

Typically, an intact or full-length antibody comprises two heavy chains and two light chains. Each heavy chain contains a heavy chain variable region (VH) and first, second and third constant regions (CH1, CH2 and CH3). Each light chain contains a light chain variable region (VL) and a constant region (CL). A full-length antibody may be of any type, such as an IgD, IgE, IgG, IgA, or IgM (or their subtypes) antibody, but not necessarily belong to any particular type. Immunoglobulins can be assigned to different types depending on their amino acid sequences of the heavy chain constant domains. Generally, immunoglobulins have five main types, i.e., IgA, IgD, IgE, IgG, and IgM, and some of these types can be further classified into subtypes (isotypes), such as IgG1, IgG2, IgG3, IgG4, IgA1, and IgA2. Heavy chain constant domains corresponding to individual immunoglobulin types are referred to as α, δ, ε, γ, and μ, respectively. Subunit structures and three-dimensional structures of different types of immunoglobulins are well known.

As used herein, the term "bispecific antibody" is an antibody having the ability to bind to two different antigens. For example, a bispecific antibody may consist of two Fc fragments and two antigen-binding portions fused thereto, respectively.

As used herein, the term "antigen-binding fragment" or "antigen-binding portion" can be used interchangeably, and refers to a portion or region of an intact antibody molecule responsible for binding to an antigen. An antigen binding domain can comprise a heavy chain variable region (VH), a light chain variable region (VL), or both. Each of a VH and a VL typically contains three complementarity determining regions, i.e., CDR1, CDR2, and CDR3.

It is well known to those skilled in the art that complementarity determining regions (CDRs, usually including CDR1, CDR2 and CDR3) are the regions of a variable region that have mostly impact on the affinity and specificity of an antibody. The CDR sequences of a VH or VL have two common definitions, i.e., the Kabat definition and the Chothia definition (see, e.g., Kabat, "Sequences of Proteins of Immunological Interest", National Institutes of Health, Bethesda, Md. (1991); Al-Lazikani et al., J. Mol. Biol. 273: 927-948 (1997); and Martin et al., Proc. Natl. Acad. Sci. USA 86: 9268-9272 (1989)). For the variable region sequences of a given antibody, the sequences of CDR regions in the VH and VL can be determined according to the Kabat definition or the Chothia definition. In some embodiments of the present application, CDR sequences are defined according to Kabat.

For the variable region sequences of a given antibody, the sequences of CDR regions in the variable region sequences can be analyzed in a variety of ways, for example, using online software Abysis (http://www.abysis.org/).

For conventional antibodies, examples of an antigen-binding fragment include, but are not limited to, (1) an Fab fragment, which can be a monovalent fragment having a VL-CL chain and a VH-CH1 chain; (2) an F(ab')$_2$ fragment, which can be a divalent fragment having two Fab' fragments linked by a disulfide bridge of the hinge region (i.e., a dimer of Fab'); (3) an Fv fragment having VL and VH domains in a single arm of an antibody; (4) a single chain Fv (scFv), which can be a single polypeptide chain consisting of a VH domain and a VL domain via a polypeptide linker; and (5) (scFv)$_2$, which can comprise two VH domains linked by a peptide linker and two VL domains that are combined with the two VH domains via a disulfide bridge.

In bispecific antibody construction, an "antigen-binding portion" includes, but is not limited to, a Fab fragment or a single chain antibody (scFv).

As used herein, the term "single chain fragment variable (scFv)" refers to an antibody of a single chain structure comprising a polypeptide chain comprising a heavy chain variable region (VH) and a light chain variable region (VL), which is generally constructed using genetic engineering techniques. A flexible linker is typically designed between the heavy chain variable region and the light chain variable region so that the heavy chain variable region and the light chain variable region can be folded into the correct conformation capable of binding to an antigen.

As used herein, the term "Fab (fragment antigen-binding) fragment", "Fab portion", or the like referred to an antibody fragment capable of binding to an antigen that are produced after treatment of an intact antibody with papain, including the intact light chain (VL-CL), the heavy chain variable region, and the CH1 fragment (VH-CH1).

As used herein, the term "monoclonal antibody" refers to an antibody from a substantially homogeneous antibody population, i.e., antibodies constituting the population are the same except for naturally occurring mutations which may be present in a small number of individual antibodies. Monoclonal antibodies described herein particularly include "chimeric" antibodies in which a portion of the heavy and/or light chain is identical or homologous to a corresponding sequence in an antibody derived from a particular species or belonging to a particular antibody type or subtype, while the remainder of the heavy and/or light chain is identical or homologous to a corresponding sequence in an antibody derived from another species or belonging to another antibody type or subtype, and also include fragments of such antibodies as long as they exhibit desired biological activity (see, U.S. Pat. No. 4,816,567; and Morrison et al., Proc. Natl. Acad. Sci. USA 81: 6851-6855 (1984)).

As used herein, the term "epitope", also referred to as an antigenic determinant (AD), refers to a particular chemical group in an antigen molecule that determines its antigen specificity. An antigen binds to its antigen receptor on the surface of a corresponding lymphocyte through an antigen epitope, thereby activating the lymphocyte and causing an immune response. An antigen also exerts its immune effects by specific binding of an epitope to a corresponding antibody or sensitized lymphocyte. The nature, number and spatial configuration of an antigenic epitope determines the specificity of an antigen.

As used herein, the term "specific binding" refers to a non-random binding reaction between two molecules, e.g., binding of an antibody to an antigen epitope.

Degenerate bases (besides conventional bases A, T, C, and G) are used in the nucleic acid sequences described herein and have the same meanings as commonly understood by those skilled in the art. For example, R represents A or G; Y represents C or T, M represents A or C; K represents G or T; S represents C or G; W represents A or T; H represents A or C or T; B represents C or G or T; V represents A or C or G; D represents A or G or T; N represents A or C or G or T.

In a first aspect, there is provided in the present application a bispecific antibody comprising two antigen-binding fragments that bind to different epitopes of rabies virus G protein, wherein the bispecific antibody has the activity of neutralizing rabies virus.

In some embodiments, one antigen-binding fragment in the bispecific antibody binds to epitope I of rabies virus G protein and the other antigen-binding fragment binds to epitope III of rabies virus G protein.

In some embodiments, the antigen-binding fragment that binds to epitope I of rabies virus G protein comprises:

HCDR1 having the amino acid sequence of RYTIN, HCDR2 having the amino acid sequence of GIIPIFGTANYAQRFQG, HCDR3 having the amino acid sequence of ENLDNSGTYYYYFSGWFDP, LCDR1 having the amino acid sequence of TGTSSDIGAYDYVS, LCDR2 having the amino acid sequence of DATKRPS, LCDR3 having the amino acid sequence of CSYAGDYTPGVV; or HCDR1 having the amino acid sequence of RYSIN, HCDR2 having the amino acid sequence of GIIPIFGTANYAQRFQG, HCDR3 having the amino acid sequence of ENLDNSGTYYYYFSGWFDP, LCDR1 having the amino acid sequence of TGTSSDIDGYDFVS, LCDR2 having the amino acid sequence of DATKRPS, LCDR3 having the amino acid sequence of CSYAGDYTPGVV; or HCDR1 having the amino acid sequence of GYTIN, HCDR2 having the amino acid sequence of GIIPIFGTANYAQRFQG, HCDR3 having the amino acid sequence of ENLDNSGTYYYYFSGWFDP, LCDR1 having the amino acid sequence of TGTSSDLGGYDFVS, LCDR2 having the amino acid sequence of DATKRPS, LCDR3 having the amino acid sequence of CSYAGDYTPGVV;

wherein the HCDR and LCDR amino acid sequences are defined according to Kabat.

In some embodiments, the antigen-binding fragment that binds to epitope III of rabies virus G protein comprises:

HCDR1 having the amino acid sequence of SYGMH, HCDR2 having the amino acid sequence of TISYDGSIKDYADSVKG, HCDR3 having the amino acid sequence of GDRTGNLDY, LCDR1 having the amino acid sequence of RASQNIRNALN, LCDR2 having the amino acid sequence of DASTRQS, LCDR3 having the amino acid sequence of QQNSEFPPT;

wherein the HCDR and LCDR amino acid sequences are defined according to Kabat.

In some embodiments, the amino acid sequence of the heavy chain variable region of the antigen-binding fragment that binds to epitope I of rabies virus G protein is as set forth in SEQ ID NO: 24, and the amino acid sequence of the light chain variable region is as set forth in SEQ ID NO: 25; or the amino acid sequence of the heavy chain variable region of the antigen-binding fragment that binds to epitope I of rabies virus G protein is as shown in SEQ ID NO: 26, and the amino acid sequence of the light chain variable region is as shown in SEQ ID NO: 27; or the amino acid sequence of the heavy chain variable region of the antigen-binding fragment that binds to epitope I of rabies virus G protein is shown in SEQ ID NO: 28, and the amino acid sequence of the light chain variable region is shown in SEQ ID NO: 29.

In some embodiments, the amino acid sequence of the heavy chain variable region of the antigen-binding fragment that binds to epitope III of rabies virus G protein is as set forth in SEQ ID NO: 1 and the amino acid sequence of the light chain variable region is as set forth in SEQ ID NO: 3.

In some embodiments, the amino acid sequence of the heavy chain variable region of the antigen-binding fragment that binds to epitope I of rabies virus G protein is as set forth in SEQ ID NO: 24, and the amino acid sequence of the light chain variable region is as set forth in SEQ ID NO: 25; and the amino acid sequence of the heavy chain variable region of the antigen-binding fragment that binds to epitope III of rabies virus G protein is as set forth in SEQ ID NO: 1, and the amino acid sequence of the light chain variable region is as shown in SEQ ID NO: 3; or the amino acid sequence of the heavy chain variable region of the antigen-binding fragment that binds to epitope I of rabies virus G protein is shown in SEQ ID NO: 26, and the amino acid sequence of the light chain variable region is shown in SEQ ID NO: 27; and the amino acid sequence of the heavy chain variable region of the antigen-binding fragment that binds to epitope III of rabies virus G protein is shown in SEQ ID NO: 1, and the amino acid sequence of the light chain variable region is as shown in SEQ ID NO: 3; or the amino acid sequence of the heavy chain variable region of the antigen-binding fragment that binds to epitope I of rabies virus G protein is shown in SEQ ID NO: 28, and the amino acid sequence of the light chain variable region is shown in SEQ ID NO: 29; and the amino acid sequence of the heavy chain variable region of the antigen-binding fragment that binds to epitope III of rabies virus G protein is shown in SEQ ID NO: 1, and the amino acid sequence of the light chain variable region is shown in SEQ ID NO: 3.

In some embodiments, the forms of the two antigen-binding fragments are independently selected from a single chain antibody (scFv) or a Fab fragment.

In some embodiments, the antigen-binding fragment that binds to epitope I of rabies virus G protein is a single chain antibody (scFv) and the antigen-binding fragment that binds to epitope III of rabies virus G protein is a Fab fragment. In some embodiments, the bispecific antibody comprises the amino acid sequence set forth in one of SEQ ID NOs: 32, 33, and 34. In some embodiments, the bispecific antibody comprises the amino acid sequences set forth in SEQ ID NO: 30 and SEQ ID NO: 31.

In a second aspect, there is provided in the present application a pharmaceutical composition comprising a bispecific antibody of the first aspect and a pharmaceutically acceptable excipient, diluent or carrier.

In some embodiments, the pharmaceutical composition is for use in the prevention or treatment of rabies.

In some embodiments, the pharmaceutical composition may further comprise one or more of a lubricant, such as talc, magnesium stearate, and mineral oil; a wetting agent; an emulsifier; a suspending agent; a preservative such as benzoic acid, sorbic acid and calcium propionate; a sweetening agent and/or a flavoring agent.

In some embodiments, the pharmaceutical composition herein may be formulated as a tablet, a pill, a powder, a lozenge, an elixir, a suspension, an emulsion, a solution, a syrup, a suppository, or a capsule.

In some embodiments, the pharmaceutical composition of the present application may be delivered using any physiologically acceptable administration route including, but not limited to, oral administration, parenteral administration, nasal administration, rectal administration, intraperitoneal administration, intravascular injection, subcutaneous administration, transdermal administration, or inhalation administration.

In some embodiments, a pharmaceutical composition for therapeutic use may be formulated for storage in a lyophilized formulation or in the form of an aqueous solution by mixing an agent with desired purity with a pharmaceutically acceptable carrier or excipient where appropriate.

In a third aspect, there is provided in the present application use of a bispecific antibody of the first aspect in the manufacture of a medicament for the prevention or treatment of rabies.

In a fourth aspect, there is provided in the present application a method of preventing or treating rabies, comprising administering to a subject in need thereof a bispecific antibody of the first aspect or a pharmaceutical composition of the second aspect.

In other aspects, there is provided in the present application a nucleic acid molecule encoding a bispecific antibody of the first aspect. In some embodiments, the nucleic acid molecule is operably linked to a regulation sequence that can be recognized by a host cell transformed with a vector.

There is also provided in the present application a vector comprising an isolated nucleic acid molecules encoding a bispecific antibody of the present application and a host cell comprising the nucleic acid molecule or vector.

In other aspects, there is provided in the present application a method of producing a bispecific antibody of the present application. In some embodiments, a method of producing a bispecific antibody comprises culturing a host cell to facilitate expression of a nucleic acid. In some embodiments, the method of producing a bispecific antibody further comprises recovering the bispecific antibody from a culture medium of the host cell.

It is to be understood that the foregoing detailed description is intended only to enable those skilled in the art to have better understanding of the present application and is not intended to cause limitations in any way. Various modifications and variations can be made to the described embodiments by those skilled in the art.

The following Examples are for purposes of illustration only and are not intended to limit the scope of the present application.

EXAMPLES

Example 1: Preparation and Verification of Monoclonal Antibodies Against Rabies Virus G Protein The inventors of the present application used inactivated rabies virus as an antigen to screen for monoclonal antibodies and identified two human monoclonal antibodies with neutralizing activity, which were named C11m and C34m, respectively. Then, the inventors completed sequence analysis of the heavy and light chain variable regions of the two monoclonal antibodies C11m and C34m.

Firstly, fully human monoclonal antibodies C34m and C11m against rabies virus G protein were prepared according to the variable region sequences of C11m and C34m, respectively. Specifically, the genes encoding the antibody heavy chain variable region C34mVH (SEQ ID NO: 1) and light chain variable region C34mVK (SEQ ID NO: 3) were cloned into a eukaryotic expression vector (such as pcDNA3.1, Invitrogen, Inc.) carrying the genes encoding human heavy chain constant region CH-IgG1 (SEQ ID NO: 5) and light chain constant region CK (SEQ ID NO: 6), respectively, thereby obtaining a C34m recombinant antibody expression vector. In addition, the genes encoding the antibody heavy chain variable region C11mVH (SEQ ID NO: 2) and light chain variable region C11mVL (SEQ ID NO: 4) were cloned into a eukaryotic expression vector (such as pcDNA3.1, Invitrogen, Inc.) carrying the genes encoding human heavy chain constant region CH-IgG1 (SEQ ID NO: 5) and light chain constant region CL (SEQ ID NO: 7), respectively, thereby obtaining a C11m recombinant antibody expression vector. The prepared C34m recombinant antibody expression vector and C11m recombinant antibody expression vector were then transfected into HEK293 cells (e.g., HEK293F cells, Invitrogen, Inc.) using liposomes (e.g., 293 fectin, Invitrogen, Inc.) or other cationic transfection reagents (e.g., PEI), respectively. The cells were cultured in suspension in serum-free mediums for 3-5 days. The culture supernatants were then harvested by centrifugation.

In addition, a single chain antibody-Fc fusion protein (scFv-Fc) against rabies virus G protein was prepared. Specifically, a flexible peptide linker GGGGGSGGGGSGGGGS (SEQ ID NO: 58) was added between the heavy and light chain variable regions of monoclonal antibodies C34m and C11m, respectively, thereby constructing single chain antibodies C34m-scFv (SEQ ID NO: 8) and C11m-scFv (SEQ ID NO: 9) in the form of VH-linker-VK. The genes encoding the single chain antibodies C34m-scFv and C11m-scFv are then cloned into eukaryotic expression vectors (such as pcDNA3.1, Invitrogen, Inc.) carrying the genes encoding the Fc segment of human IgG1 (Fc, SEQ ID NO: 10) or the Fc segment of murine IgG2a (mFc, SEQ ID NO: 11), respectively, thereby obtaining a single chain antibody C34m-scFv-Fc/mFc recombinant antibody expression vector and a single chain antibody C11m-scFv-Fc/mFc recombinant antibody expression vector. The prepared single chain antibody C34m-scFv-Fc/mFc recombinant antibody expression vector and the single chain antibody C11m-scFv-Fc/mFc recombinant antibody expression vector were transfected into HEK293 cells (such as HEK293F, Invitrogen, Inc.) using liposomes (such as 293fectin, Invitrogen, Inc.) or other cationic transfection reagents (such as PEI), respectively. The cells were cultured in suspension in serum-free mediums for 3-5 days. The culture supernatants were then harvested by centrifugation.

The culture supernatant of the harvested human IgG1 fully human monoclonal antibodoes or single-chain antibody-Fc fusion proteins against rabies virus G protein were were subjected to one-step purification using Protein A/G affinity chromatography columns (e.g., Mabselect SURE, GE, Inc.). The preservation buffers of recombinant antibodies were then replaced with PBS buffers (pH 7.0) using a desalting column (such as Hitrap desalting, GE, Inc.) or other suitable buffers. If necessary, the antibody samples can be sterilized by filtration and then stored in aliquots at −20° C.

Example 2: Validation of Binding of Monoclonal Antibodies to Non-Competitive Epitopes of Rabies Virus G Protein 96-well ELISA plates were coated with prepared inactivated rabies virus (prepared using MRC-5 cells) (1 IU/mL, 100 μL/well) overnight at 4° C. After blocking with a blocking solution (2% milk-PBST buffer) at 37° C. for 1 hour, the fully human monoclonal antibodies C34m and C11m prepared in Example 1 were added at an equimolar initial concentration (200 nM) and a series of 3-fold gradient dilutions (totally 8 concentrations), respectively, and incubated at 37° C. for 1 hour. The ELISA plates were washed with a PBST buffer, and a HRP anti-human IgG (a secondary antibody) was added and incubated at 37° C. for 1 hour. The ELISA plates were then washed with a PBST buffer, and an OPD substrate developing solution was added. After incubation for 5-10 minutes, the development was terminated with 1 M $H_2SO_4$ solution, and the optical density values were determined using a microplate reader at 490 nm/630 nm dual wavelength. The ELISA assay results (FIG. 1) show that both fully human monoclonal antibodies C34m and C11m are able to bind to the coated inactivated rabies virus with comparable binding capacity.

Figure 2:
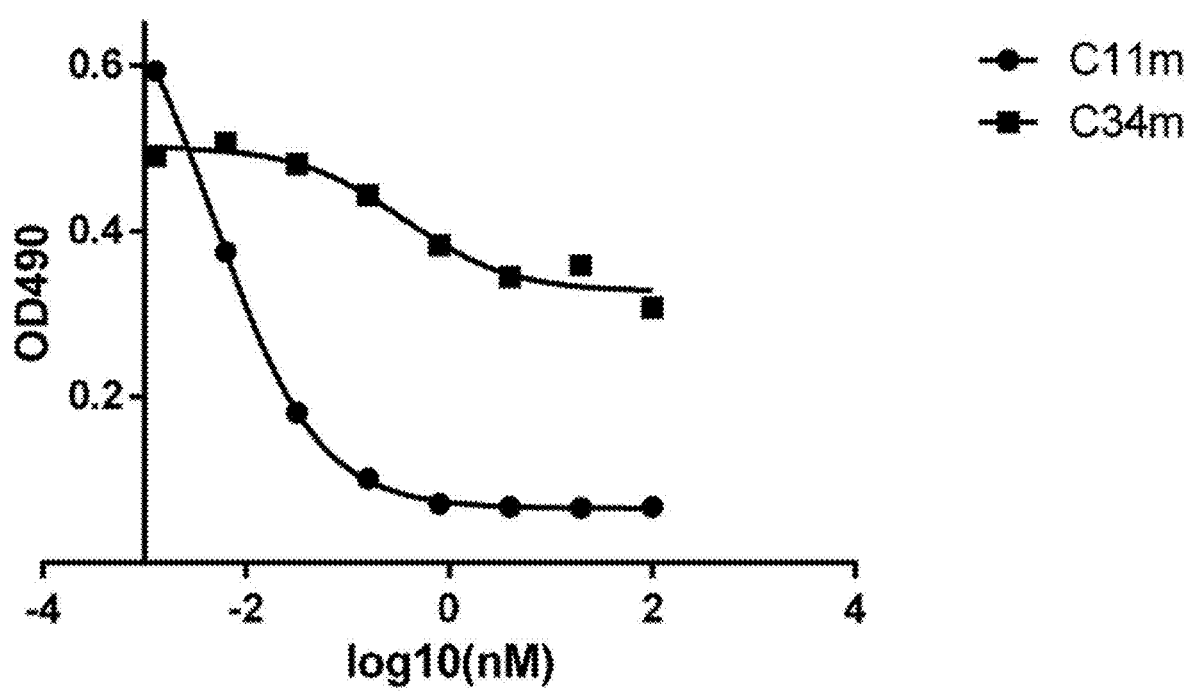
FIG. 2 shows the ELISA assay result of inhibition of binding of phage-C11m to inactivated rabies virus by fully human monoclonal antibodies C34m and C11m.
Figure 3:
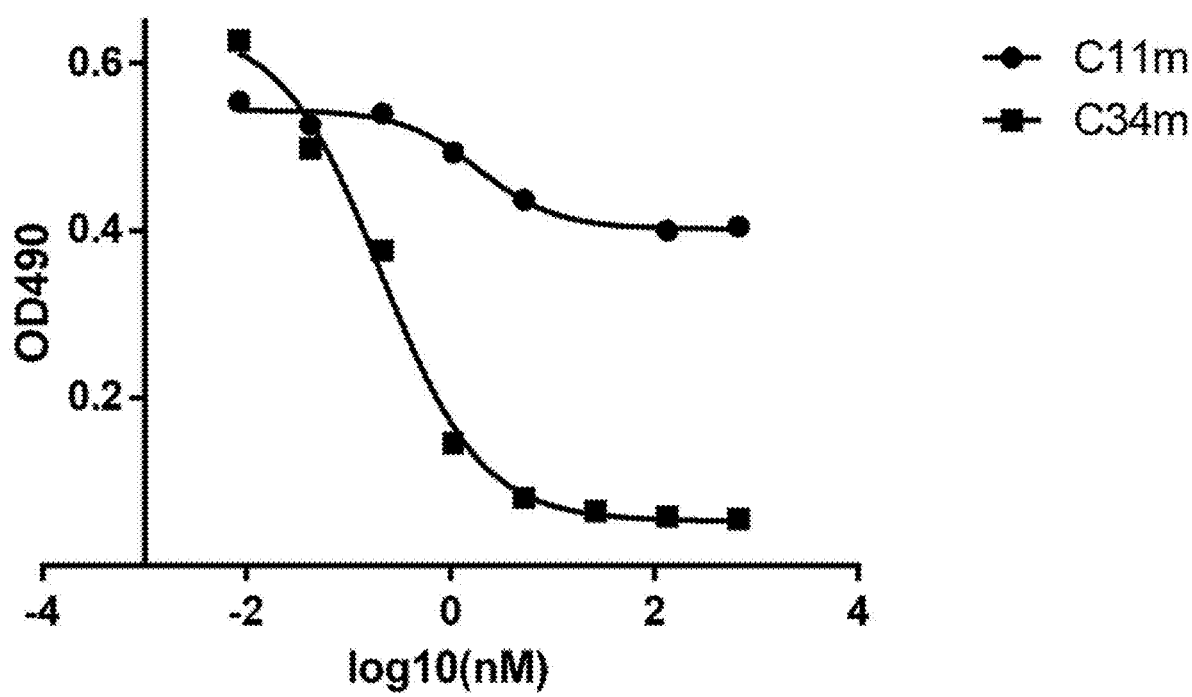
FIG. 3 shows the ELISA assay result of inhibition of binding of phage-C34m to inactivated rabies virus by fully human monoclonal antibodies C34m and C11m.

The genes encoding the heavy chain variable regions and the light chain variable regions of the fully human monoclonal antibodies C34m and C11m were cloned into the two-vector display systems pADK-S and pAG-S, respectively (see Example 4.1 in Chinese Patent Application No. 201510097117.0 for detailed experimental protocols). Phage-C34m and phage-C11m displaying single species of Fab were prepared and purified, and frozen at −20° C. for use after titration determination. 96-well ELISA plates were coated with the prepared inactivated rabies virus (prepared using MRC-5 cells) (1 IU/mL, 100 μL/well) overnight at 4° C. The fully human monoclonal antibodies C34m and C11m prepared in Example 1 at an equimolar initiation concentration (200 nM) were diluted with phage-C34m and phage-C11m at a fixed concentration (1×10E12 cfu/mL) using 3-fold gradients (totally 8 concentrations) respectively, then added to 96-well plates at 100 pt/well and incubated at 37° C. for 1 hour. Inhibition of binding of phage-C34m and phage-C11m to inactivated rabies virus by the fully human monoclonal antibodies C34m and C11m was detected using HRP anti-M13-IgG (a secondary antibody). The ELISA assay results (FIGS. 2 and 3) show that the fully human monoclonal antibody C11m completely blocks the binding of phage-C11m to the inactivated rabies virus, and the fully human monoclonal antibody C34m does not completely block the binding of phage-C11m to the inactivated rabies virus. The fully human monoclonal antibody C34m completely blocks the binding of phage-C34m to the inactivated rabies virus, and the fully human monoclonal antibody C11m cannot block the binding of phage-C34m to the inactivated rabies virus. These results indicate that the fully human monoclonal antibodies C34m and C11m have non-competitive binding epitopes on rabies virus G protein.

Example 3: Epitope Verification of Monoclonal Antibodies Against Rabies Virus G Protein Genes encoding the heavy chain variable region CR57VH (SEQ ID NO: 12) of monoclonal antibody CR57 against epitope I of rabies virus G protein and the heavy chain variable region CR4098VH (SEQ ID NO: 13) of monoclonal antibody CR4098 against epitope III of rabies virus G protein (Bakker, A. B. et al. Novel human monoclonal antibody combination effectively neutralizing natural rabies virus variants and individual in vitro escape mutants. J. Virol. 79, 9062-9068; and U.S. Pat. No. 9,005,624 B2) were respectively cloned into eukaryotic expression vectors (such as pcDNA3.1, Invitrogen, Inc.) carrying a gene encoding the murine IgG2a heavy chain constant region (CH-mIgG2a, SEQ ID NO: 14). A gene encoding the light chain variable region CR57VL (SEQ ID NO: 15) of CR57 was cloned into a eukaryotic expression vector (such as pcDNA3.1, Invitrogen, Inc.) carrying a gene encoding a murine light chain constant region mCL (SEQ ID NO: 17), and a gene encoding the light chain variable region CR4098VK (SEQ ID NO: 16) of CR4098 cloned into a eukaryotic expression vector (such as pcDNA3.1, Invitrogen, Inc.) carrying a murine light chain constant region mCK (SEQ ID NO: 18). Chimeric antibodies CR57-mIgG2a based on CR57 and CR4098-mIgG2a based on CR4098 were constructed according to the method of Example 1, respectively.

Figure 4:
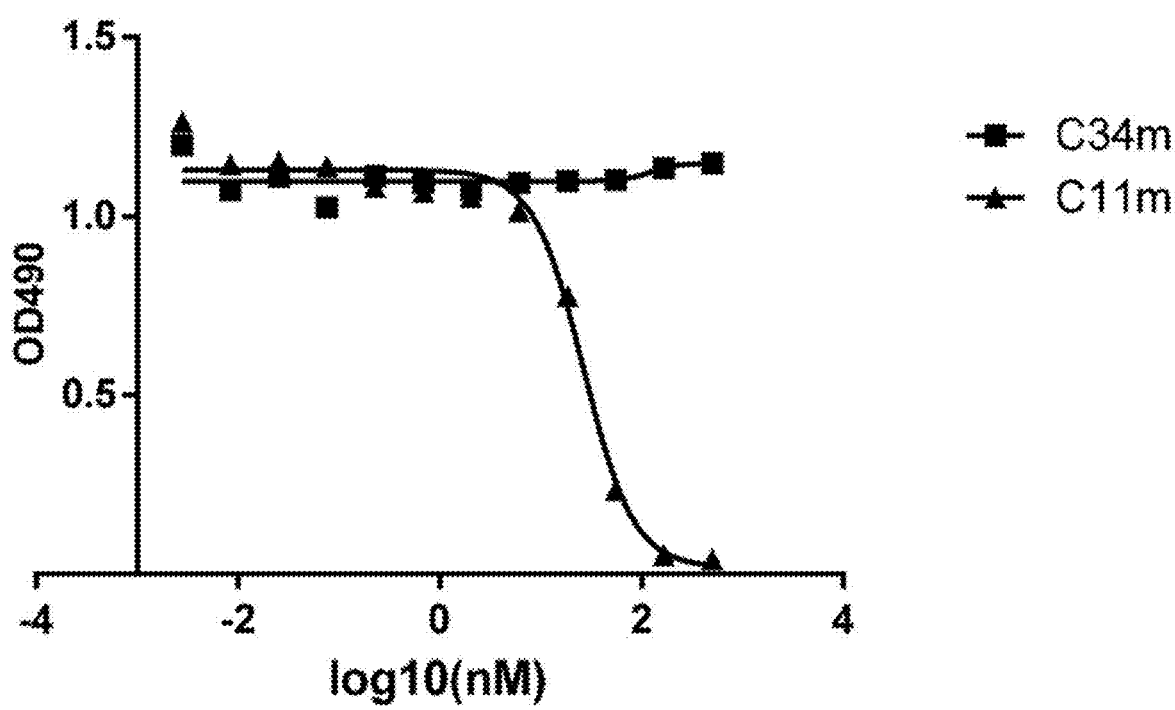
FIG. 4 shows the ELISA assay result of inhibition of binding of chimeric antibody CR57-mIgG2a to inactivated rabies virus by fully human monoclonal antibodies C11m and C34m.
Figure 5:
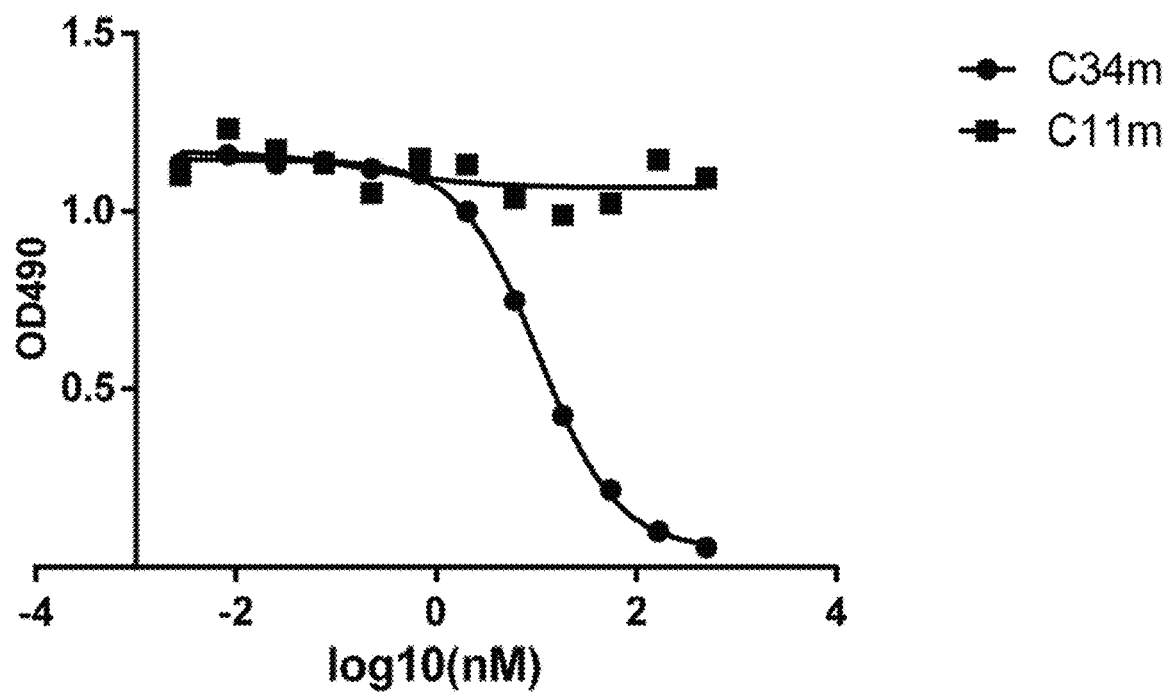
FIG. 5 shows the ELISA assay result of inhibition of binding of chimeric antibody CR4098-mIgG2a to inactivated rabies virus by fully human monoclonal antibodies C11m and C34m.

96-well ELISA plates (1 IU/mL, 100 μL/well) were coated with the prepared inactivated rabies virus (prepared using MRC-5 cells) overnight at 4° C. The fully human monoclonal antibodies C11m and C34m at an equimolar initiation concentration (200 nM) were diluted with chimeric antibodies CR57-mIgG2a and CR4098-mIgG2 at a fixed concentration (2.5 μg/mL) using 3-fold gradients (totally 12 concentrations), respectively, added to 96-well plates at 100 pt/well and incubated at 37° C. for 1 hour. HRP anti-murine IgG (a secondary antibody) was used to detect the inhibition of binding ability of the chimeric antibodies CR57-mIgG2a and CR4098-mIgG2a to the inactivated rabies virus by the fully human monoclonal antibodies C11m and C34m, respectively. The ELISA assay results (FIG. 4, FIG. 5) show that the fully human monoclonal antibody C11m competes with the chimeric antibody CR57-mIgG2a for binding to rabies virus G protein, but not with the chimeric antibody CR4098-mIgG2a, indicating that the fully human monoclonal antibody C11m specifically binds to epitope I of rabies virus G protein. The fully human monoclonal antibody C34m competes with the chimeric antibody CR4098-mIgG2a for binding to rabies virus G protein, but not with the chimeric antibody CR57-mIgG2a, indicating that the fully human monoclonal antibody C34m specifically binds to epitope III of rabies virus G protein.

Example 4: Screening for C11m-scFv Mutants with More Suitable pI Values

Bispecific antibodies based on the KIH strategy are better in forming heterodimers, but it is still difficult to completely prevent the formation of homodimers in large-scale preparation processes. Ion exchange chromatography (IEC) is commonly used for removing impurities after the one-step purification using Protein A in a bispecific antibody purification process. The retention time of s homodimer in the ion exchange resin depends on the isoelectric point (pI) of the antibody molecule, so that the efficiency of the downstream processes in antibody preparation can be improved by changing the isoelectric point.

The gene encoding the single chain antibody C11m-scFv prepared in Example 1 was cloned into the vector pAD-scFv-s (see Example 1.3 in Chinese Patent Application No. 201510097117.0 for detailed experimental protocols) to obtain the recombinant expression vector pADscFv-C11m-scFv. Mutations were introduced in the CDR regions of the recombinant expression vector pADscFv-C11m-scFv using overlap PCR techniques, thereby constructing a C11m-scFv mutant library with a library capacity of more than 4.6×

10E6. The core primers required in amplification are shown in Table 1. The C11m-scFv mutant library was screened for three rounds with the inactivated rabies virus (prepared using MRC-5 cells) as the antigen. Finally, three mutants S1C10-scFv (SEQ ID NO: 21), S2A1-scFv (SEQ ID NO: 22) and S2E3-scFv (SEQ ID NO: 23) with improved biding properties and expectedly reduced pI values (http://www.bioinformatics.org/sms2/protein_iep.html) were identified. PI values for individual mutants are shown in Table 2.

Figure 6:
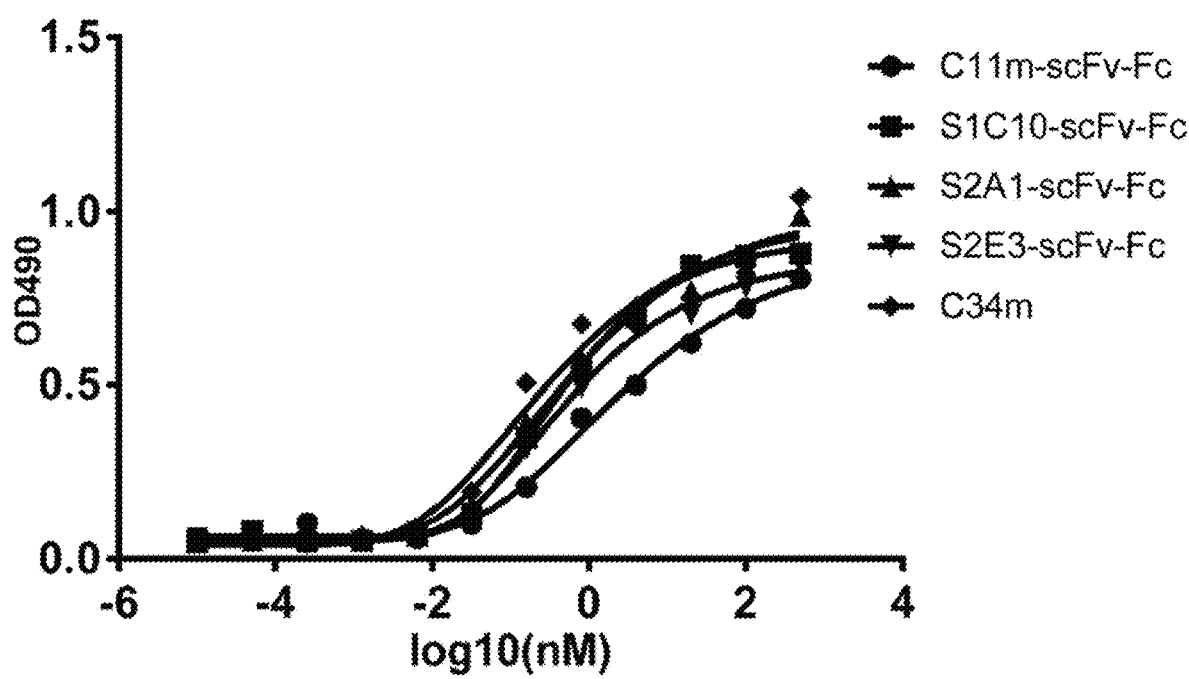
FIG. 6 shows the ELISA assay result of binding capacity of C11m-scFv-Fc single chain antibody-Fc fusion protein, three single chain antibody-Fc fusion proteins comprising C11m-scFv mutants, and the fully human monoclonal antibody C34m to inactivated rabies virus.
Figure 7:
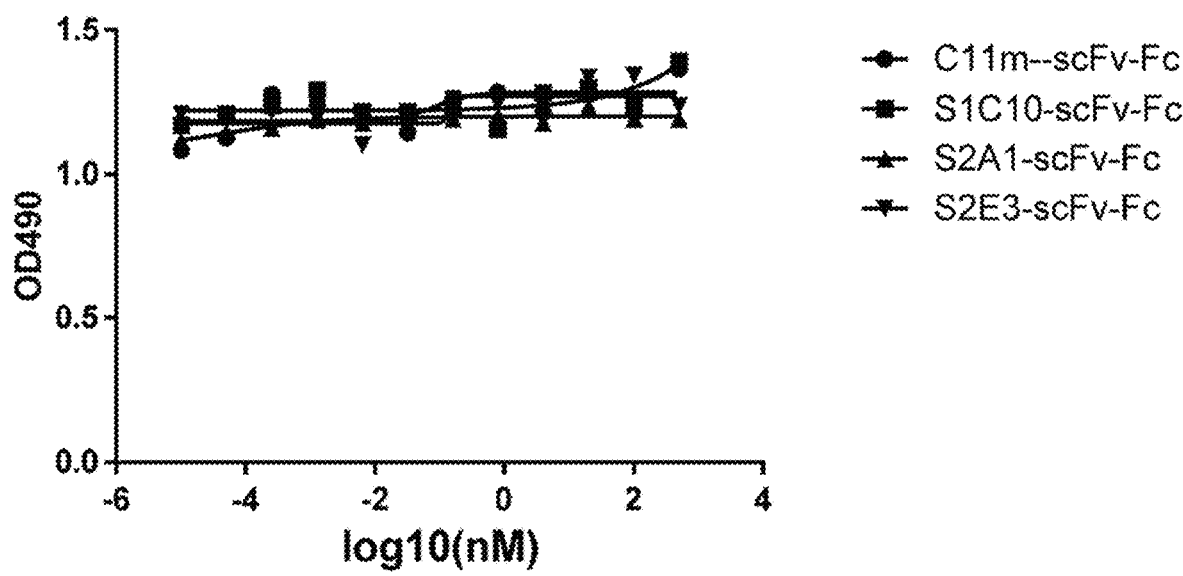
FIG. 7 shows the ELISA assay result of inhibition of binding of chimeric antibody C34m-mIgG2a to inactivated rabies virus by C11m-scFv-Fc single chain antibody-Fc fusion protein and threes ingle chain antibody Fc fusion proteins comprising C11m-scFv mutants.
Figure 8:
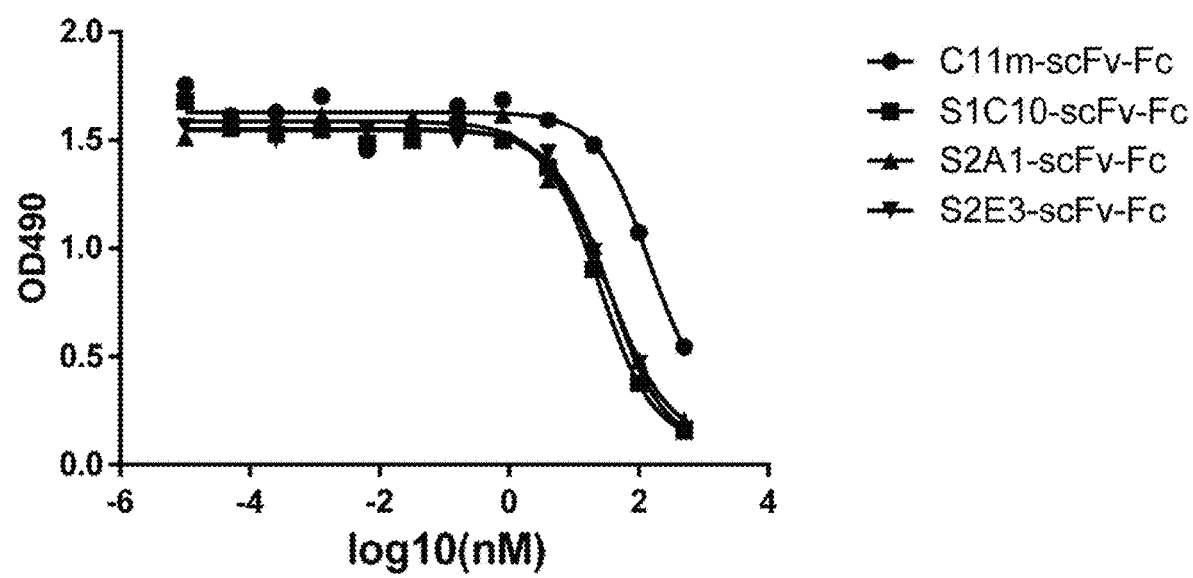
FIG. 8 shows the ELISA assay result of inhibition of binding of the chimeric antibody C11m-mIgG2a to inactivated rabies virus by the C11m-scFv-Fc single chain antibody-Fc fusion protein and three single chain antibody-Fc fusion proteins comprising C11m-scFv mutants.

According to the method in Example 1, single chain antibody-Fc fusion proteins (scFv-Fc) S1C10-scFv-Fc, S2A1-scFv-Fc and S2E3-scFv-Fc having the above three mutants fused to the Fc segment of human IgG1 were prepared. C34m chimeric antibody C34m-mIgG2a with fused murine IgG2a heavy chain constant region (CH-mIgG2a) and light chain constant region (mCK), and C11m chimeric antibody C11m-mIgG2a with fused murine IgG2a heavy chain constant region (CH-mIgG2a) and light chain constant region (mCL) were also prepared for functional analysis. According to methods in Example 2 and Example 3, determination of binding capabilities for rabies virus G protein and non-competitive epitope verifications of single chain antibody-Fc fusion proteins of three C11m-scFv mutants were performed, respectively. The ELISA assay results are shown in FIG. 6, FIG. 7 and FIG. 8, which show that the binding capabilities for rabies virus G protein of the single-chain antibody-Fc fusion proteins of the three mutants are significantly improved and comparable to that of the fully human monoclonal antibody C34m. The single chain antibody-Fc fusion protein C11m-scFv-Fc and the single chain antibody-Fc fusion proteins of the three C11m-scFv mutants bind to a non-competitive epitope on rabies virus G protein with respect to C34m-mIgG2a. The single-chain antibody-Fc fusion protein C11m-scFv-Fc and the single-chain antibody-Fc fusion proteins of the three C11m-scFv mutants compete with C11m-mIgG2a for binding to an epitope on rabies virus G protein.

TABLE 1

Core primers required to construct the C11m-scFv mutant library

| Primer Name | Primer Sequence |
| --- | --- |
| PWM08-C11m-scFv-F11 | ccagccatggcgcaggtgcagctggtgc (SEQ ID NO: 59) |
| PWM08-C11m-scFv-R11 | ctggggcctgccgcacccagyyganasy awatbygyyawaggtgccgccgctggcc ttgc (SEQ ID NO: 60) |
| PWM08-C11m-scFv-F12 | tgggtgcggcaggcccag (SEQ ID NO: 61) |
| PWM08-C11m-scFv-R12 | tgctgctgataccagctcacawagyyaw aabcabcgangtcgctgctggtgccg (SEQ ID NO: 62) |
| PWM08-C11m-scFv-F13 | gtgagctggtatcagcagca (SEQ ID NO: 63) |
| PWM08-C11m-scFv-R13 | gatgtgcggccgccaggacggtaagctt ggtg (SEQ ID NO: 64) |

TABLE 2

PI values of C11m-scFv and its mutants

| Antibody Name | pI Value |
| --- | --- |
| C11m-scFv | 7.38 |
| S1C10sc-Fv | 7.13 |
| S2A1-scFv | 6.90 |
| S2E3-scFv | 6.90 |

Example 5: Preparation of Bispecific Antibodies

Antigen-binding fragments for epitope I and III of rabies virus G protein were designed as an scFv form and a Fab form, respectively, to construct human IgG1 heterodimers based on the KIH (Knob-Into-Hole) technology. That is, the C34m antigen-binding fragment in a Fab form was fused to the N-terminus of an Fc segment containing the Knob mutation (FcK, SEQ ID NO: 19), and the C11m mutant-derived antigen-binding fragments in scFv forms were fused to the N-terminus of an Fc segment containing a Hole mutation (FcH, SEQ ID NO: 20), thereby constructing a bispecific antibody against rabies virus G protein.

The three constructed eukaryotic expression vectors expressing S1C10-scFv-FcH, C34mVH-IgG1K and C34mVK-CK, respectively, were co-transfected into HEK293F cells using liposomes, and the cells were cultured in suspension in a serum-free medium for 3-5 days. The culture supernatant was harvested by centrifugation. The bispecific antibodoes in the culture supernatant were purified using a Protein A/G affinity chromatography column (e.g., Mabselect SURE, GE Inc.). The recombinant antibody preservation buffer was then replaced with PBS buffer (pH 7.0) using a desalination column (e.g., Hitrap desaulting, GE Inc.) or other suitable buffers. The desalted protein solution was purified by a size exclusion chromatography (SEC) using Superdex 200 (GE), thereby obtaining the bispecific antibody S1C10-scFv-FcH+C34m-IgG1K. If necessary, the antibody samples can be sterilized by filtration and then stored in aliquots at −20° C.

Similarly, two bispecific antibodies, S2A1-scFv-FcH+C34m-IgG1K and S2E3-scFv-FcH+C34m-IgG1K, were prepared.

Figure 9:
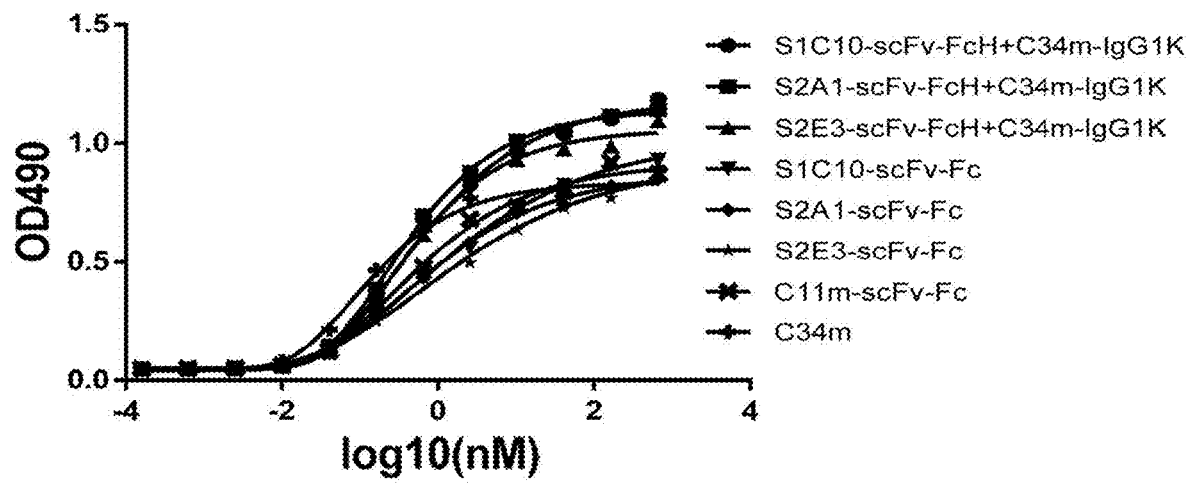
FIG. 9 shows the ELISA assay result of binding capacity of individual anti-rabies virus G protein antibodies to inactivated rabies virus.

Example 6: Functional Validation of Bispecific Antibodies 96-well ELISA plates were coated with prepared inactivated rabies virus (prepared using MRC-5 cells) (1 IU/mL, 100 μL/well) overnight at 4° C. After blocking with a blocking solution (2% milk-PBST buffer) for 1 hour at 37° C., anti-rabies virus G protein bispecific antibodies (S1C10-scFv-FcH+C34m-IgG1K, S2A1-scFv-FcH+C34m-IgG1K, S2E3-scFv-FcH+C34m-IgG1K, S1C10-scFv-Fc, S2A1-scFv-Fc, S2E3-scFv-Fc, C11m-scFv-Fc, and C34m) were added at an equimolar initial concentration (200 nM) and a series of 3-fold gradient dilutions (totally 12 concentrations), respectively, and incubated at 37° C. for 1 hour. The ELISA plates were washed with a PBST buffer, and a HRP anti-human IgG (a secondary antibody) was added and incubated at 37° C. for 1 hour. The ELISA plates were then washed with a PBST buffer, and an OPD substrate developing solution was added. After incubation for 5-10 minutes, the development was terminated with 1 M $H_2SO_4$ solution, and the optical density values were determined using a microplate reader at 490 nm/630 nm dual wavelength. The ELISA assay results (FIG. 9) show that the capacities of the bispecific antibodies in binding to the inactivated rabies virus were better than those of the single chain antibody-Fc fusion proteins and the fully human monoclonal antibody C34m.

Figure 10:
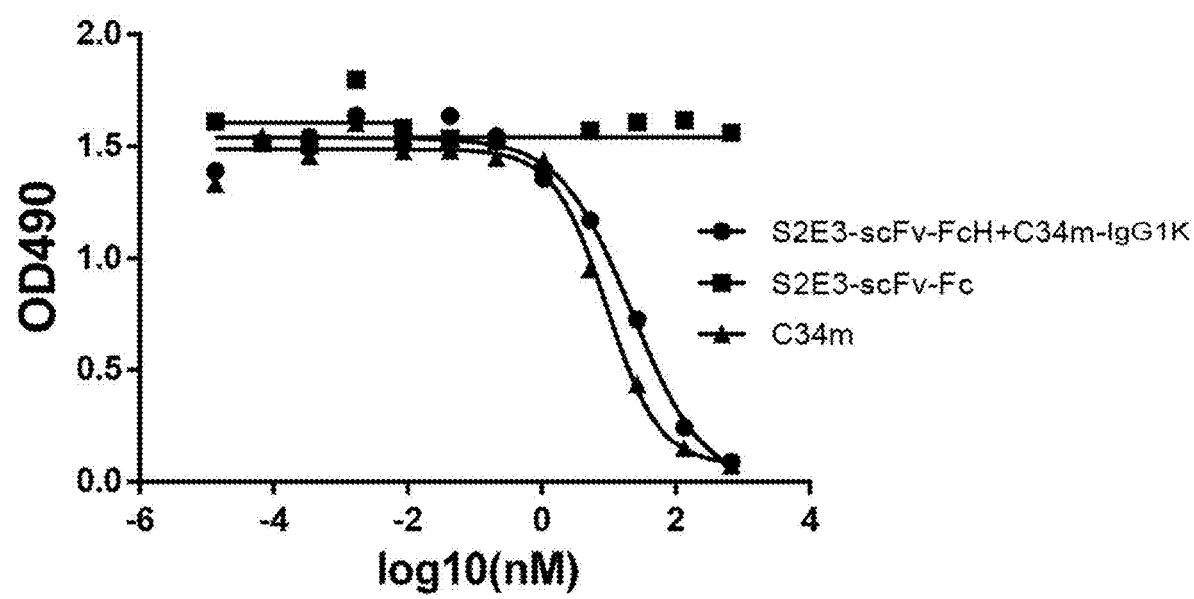
FIG. 10 shows the ELISA assay result of inhibition of binding of the chimeric antibody C34m-mIgG2a to inactivated rabies virus by the bispecific antibody S2E3-scFv-FcH+C34m-IgG1K, the single chain antibody-Fc fusion protein S2E3-scFv-Fc and the fully human monoclonal antibody C34m.
Figure 11:
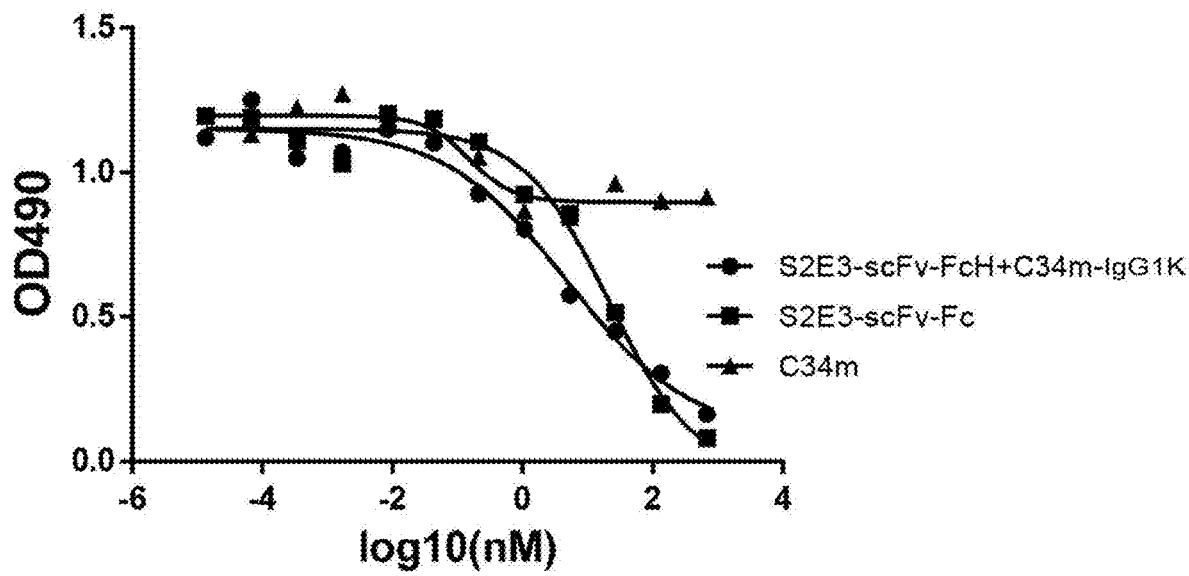
FIG. 11 shows the ELISA assay result of inhibition of binding of the chimeric protein S2E3-scFv-mFc to inactivated rabies virus by the bispecific antibody S2E3-scFv-FcH+C34m-IgG1K, the single chain antibody-Fc fusion protein S2E3-scFv-Fc and the fully human monoclonal antibody C34m.

The single-chain antibody S2E3-scFv having a lower pI value was selected, and prepared into chimeric protein S2E3-scFv-mFc following the procedures in Example 1. The bispecific antibody S2E3-scFv-FcH+C34m-IgG1K, single-chain antibody-Fc fusion protein S2E3-scFv-Fc, and fully human monoclonal antibody C34m at an equimolar initial concentration (200 nM) were diluted with C34m-mIgG2a and S2E3-scFv-mFc at a fixed concentration (2.5 μg/mL) using 3-fold gradients (totally 12 concentrations) respectively, then added to 96-well plates at 100 μL/well and incubated at 37° C. for 1 hour. HRP anti-murine IgG (a secondary antibody) was used in detection of binding signals. The ELISA assay results (FIG. 10 and FIG. 11) show that the bispecific antibody S2E3-scFv-FcH+C34m-IgG1K is capable of inhibiting the binding of the chimeric antibody S2E3-scFv-mFc and the chimeric antibody C34m-mIgG2a to rabies virus vaccine. That is, the bispecific antibody S2E3-scFv-FcH+C34m-IgG1K against rabies virus G protein works on two non-competitive binding epitopes, and is capable of binding both epitope I and the epitope III of rabies virus G protein.

Example 7: Antibody Titer Assay Based on Rapid Fluorescence Focus Inhibition Test (RFFIT) on Anti-Rabies Virus Neutralizing Antibodies According to the Rapid Fluorescent Focus Inhibition Test (RFFIT) on anti-rabies virus neutralizing antibodies, standard serum (0.5 IU/mL) and pre-diluted test antibodies (bispecific antibody S2E3-scFv-FcH+C34m-IgG1K, single chain antibody-Fc fusion S2E3-scFv-Fc and fully human monoclonal antibody C34m, 10 μg/mL) were serially diluted in 3-fold gradients. Standard serum or test antibodies were added in 96-well plates (50 μL/well) with triplicate for each sample. Rabies virus to be neutralized diluted in an appropriate proportion was added to each well. Wells without standard serum or test antibody were set as virus dilution control wells, and wells without standard serum, test antibody or rabies virus were set as cell control wells. The plates were incubated at 37° C. for 1 hour, 50 μL of BSR cells (1×10E6 cells/ml) were added to each well, and the plates were incubated at 37° C. in a 5% $CO_2$ incubator. After 24 hours 50 μL of cold acetone was added to fix for 30 min and then washed with a PBST buffer. 50 μL of rabies virus fluorescent antibody working solution was added to each well and the plates were incubated at 37° C. for 30 min. After washing with a PBS buffer, glycerol (80%) was added to each well, fluorescence staining was performed under an inverted fluorescence microscope, and the titers of the test samples were calculated according to the Reed-Muench method.

Three antibodies were assayed using the standard rabies virus attack strain CVS-11, and the results are shown in Table 3. The results indicate that the bispecific antibody S2E3-scFv-FcH+C34m-IgG1K, the single chain antibody-Fc fusion protein S2E3-scFv-Fc and the fully human monoclonal antibody C34m all have good neutralizing activity.

TABLE 3

Measurement of antibody titers by RFFIT

| Antibody | Measurement (IU/mg) | Average value (IU/mg) |
|---|---|---|
| S2E3 - scFv-FcH + C34m-IgG1K | 1810 | 1738 |
| | 1745 | |
| | 1660 | |
| S2E3 - scFv-Fc | 1745 | 1837 |
| | 1915 | |
| | 1850 | |
| C34m | 2095 | 2107 |
| | 2260 | |
| | 1965 | |

Example 8: Anti-Rabies Virus Antibodies' Protection to Golden Hamsters from Lethal Attack by Rabies Virus The protective effect of each group of antibodies was determined by post-exposure immunoglobulin administration in golden hamsters injected with a lethal dose of rabies virus, and was compared with commercial products.

Golden hamsters were attacked with standard rabies virus attack strain CVS-11 (6.67 IgLD50/mL, 0.2 ml/animal) on their right hind legs. Anti-rabies virus antibodies were administered at the same sites 24 hours later. Grouping was done according to injection doses (IU/kg). The bispecific antibody S2E3-scFv-FcH+C34m-IgG1K test was divided into three groups according to injection doses of 5 IU/kg, 20 IU/kg and 30 IU/kg. The tests of single chain antibody-Fc fusion protein S2E3-scFv-Fc, the fully human monoclonal antibody C34m and the human rabies virus immunoglobulin of commercial origin (Tonrol Biopharmaceutical Co., Ltd.) (referred to hereafter as Tonrol immunoglobulin) were respectively divided into two groups according to injection doses of 5 IU/kg and 20 IU/kg. Golden hamsters not injected with anti-rabies virus antibody served as a control group. There were a total of 10 groups with 9 animals per group. Each sample was diluted with a PBS buffer according to the weighing results of the golden hamsters and, for convenience of injection, the final injection volume per animal was 100 μL.

The experimental results are shown in Table 4. All golden hamsters in the control group died of rabies within 2 weeks of the attack, while the golden hamsters in the treatment group had higher survival rates. The protective effects of the anti-rabies virus antibodies of the present application were comparable to that of Tonrol immunoglobulin injection.

TABLE 4

Experimental results of post-exposure protection in golden hamsters

| | Group | IU/kg | Survival rate |
|---|---|---|---|
| 1 | Tonrol immunoglobulin | 5 | 44%, 4/9 |
| 2 | | 20 | 78%, 7/9 |
| 3 | S2E3-scFv-FcH + C34m-IgG1K | 5 | 56%, 5/9 |
| 4 | | 20 | 78%, 7/9 |
| 5 | | 30 | 89%, 8/9 |
| 6 | C34m | 5 | 44%, 4/9 |
| 7 | | 20 | 78%, 7/9 |
| 8 | S2E3 - scFv-Fc | 5 | 44%, 4/9 |
| 9 | | 20 | 67%, 6/9 |
| 10 | Control group | / | 0%, 0/9 |

Example 9 Identification of Binding Epitope of Antibodies Against Rabies Virus G Protein To identify the recognition epitopes of the fully human monoclonal antibody C34m having rabies virus neutralizing activity and the single chain antibody-Fc fusion protein S2E3-scFv-Fc against derived from the C11m-scFv mutant, the effect of amino acid substitutions in rabies virus glycoprotein neutralizing epitopes I-III on the G protein binding of anti-rabies virus antibodies was tested. Reports have shown that mutation of any one of epitopes I-III of rabies virus G protein enables the mutant epitope of rabies virus G protein to escape recognition of an antibody that binds to the epitope. The present Example selected a single point mutation in the amino acids of neutralizing epitopes I and III of the wild-type G protein of rabies virus strain CVS-11 to obtain an amino acid sequence (Novel rabies virus-neutralizing epitope recognized by human monoclonal antibody: Fine mapping and escape mutant analysis; Rabies virus: Effect on pathogenicity and sequence characterization of rabies virus mutations affecting antigenic site III of the glycoprotein).

According to conventional molecular biological techniques, the extracellular domain genes encoding the wild-type rabies virus strain CVS-11 G protein GCVS11 (SEQ ID NO: 35) and its epitope I mutant GCVS11-G229E (SEQ ID NO: 36) and epitope III mutant GCVS11-I338T (SEQ ID NO: 37) are obtained by PCR amplifications, and their C-termini are fused to a gene encoding the trimeric domain CCD of human coronaprotein 1A (SEQ ID NO: 38) respectively, to ensure that the secreted glycoproteins well formed trimers, and maintained their native protein conformation and immunogenicity. The obtained genes encoding the fusion proteins having the extracellular regions of the rabies virus G protein or two mutants (G229E and I338T) and CCD were respectively cloned into eukaryotic expression vectors carrying His tags at the C-terminus (such as pcDNA3.1, Invitrogen, Inc.), and the prepared recombinant antigen expression vectors were respectively transfected into HEK293 cells using liposomes (such as 293 fectin, Invitrogen, Inc.). The cells were cultured in suspension in a serum-free medium for 3-5 days, and the culture supernatants were harvested by centrifugal filtration. The resulting culture supernatant was concentrated about 10-fold using an ultrafiltration centrifuge tube and stored at −80° C. for later use.

96-well ELISA plates were coated with the prepared fully human monoclonal antibody C34m and the single chain antibody-Fc fusion protein S2E3-scFv-Fc (5 μg/mL, 100 Oven), respectively, at 4° C. overnight. After blocking with a blocking solution (2% milk-PBST buffer) at 37° C. for 1 hour, the concentrates of the resulting fusion proteins GCVS11-CCD-His (SEQ ID NO: 39), GCVS11-G229E-CCD-His (SEQ ID NO: 40), GCVS11-I338T-CCD-His (SEQ ID NO: 41) was subjected to 3-fold gradient dilutions (a total of 11 concentrations) and added to 96-well plates coated with C34m or S2E3-scFv-Fc (100 μL/well). The plates were incubated at 37° C. for 1 hour. Binding signals were detected using HRP-labeled anti-His-tag antibodies (a secondary antibody).

Figure 12A:
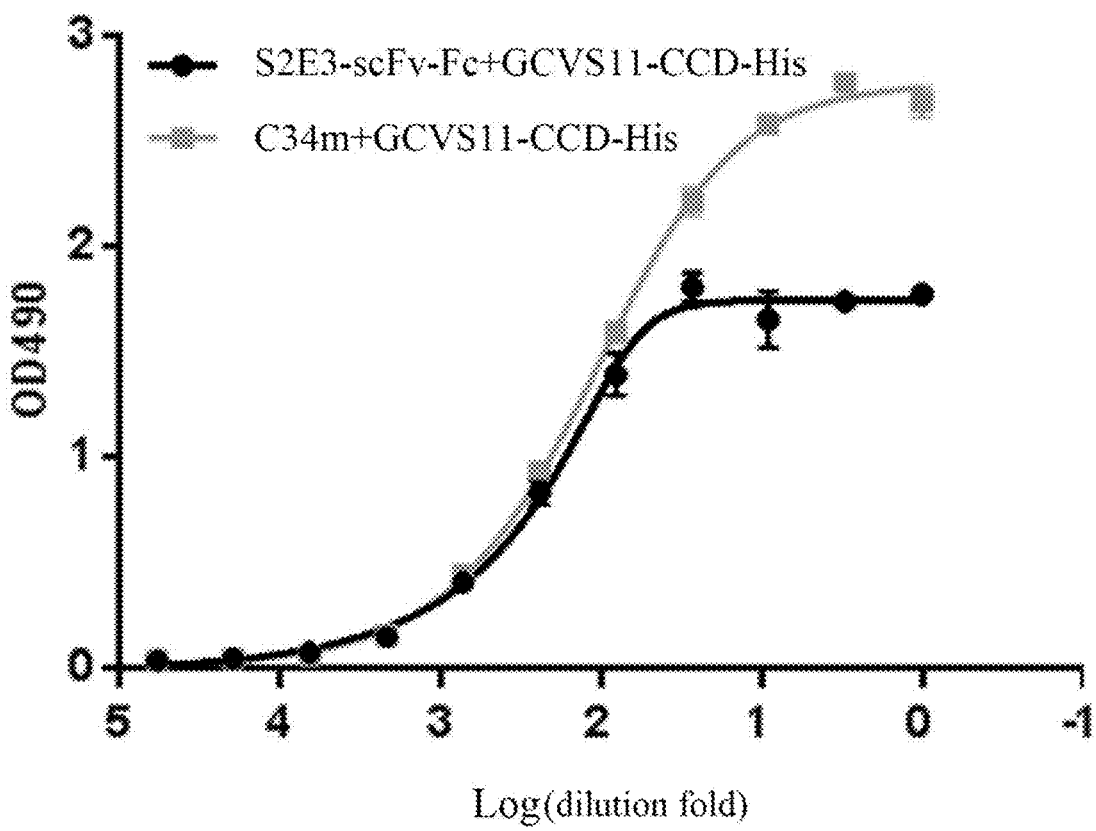
Figures 12B, 12C:
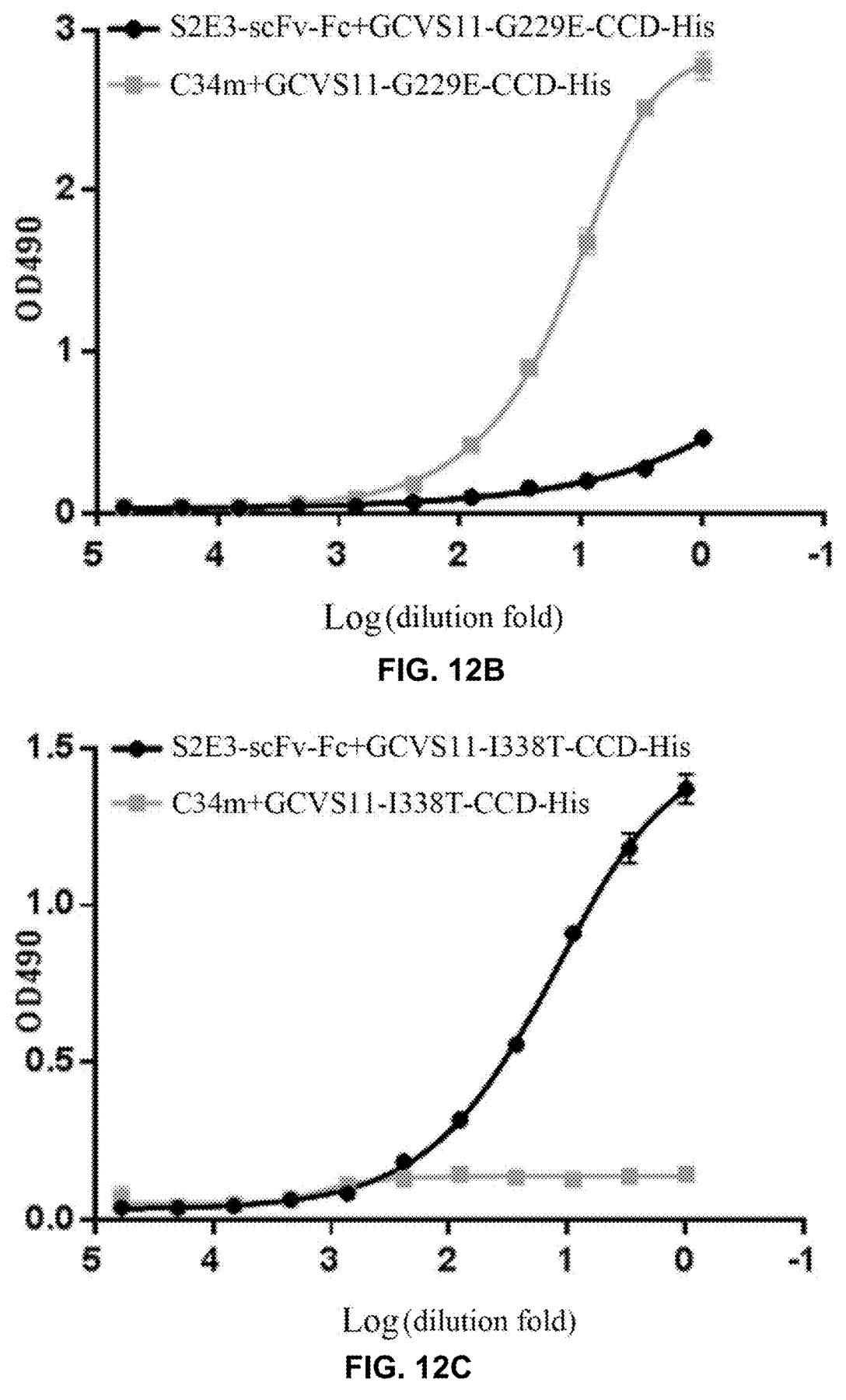

The ELISA assay results (FIGS. 12A, 12B, 12C) show that C34m and S2E3-scFv-Fc have comparable capabilities of binding to the fusion protein GCVS11-CCD-His (FIG. 12a). The binding capability of S2E3-scFv-Fc to the fusion protein GCVS11-G229E-CD-His is significantly lower than that of C34m (FIG. 12B), indicating that the binding epitope of S2E3-scFv-Fc is epitope I of rabies virus G protein. Similarly, the binding capacity of C34m to the fusion protein GCVS11-I338T-CCD-His is significantly lower than that of S2E3-scFv-Fc (FIG. 12C), indicating that the binding epitope of C34m is epitope III of rabies virus G protein.

What is claimed is:

1. A bispecific antibody comprising two antigen-binding fragments that bind to epitope I and epitope III of rabies virus G protein respectively, wherein the bispecific antibody has the activity of neutralizing rabies virus, wherein the antigen-binding fragment that binds to epitope I of rabies virus G protein comprises:

HCDR1 having the amino acid sequence of RYTIN (SEQ ID NO: 42), HCDR2 having the amino acid sequence of GIIPIFGTANYAQRFQG (SEQ ID NO: 43), HCDR3 having the amino acid sequence of ENLDNSGTYYYYFSGWFDP (SEQ ID NO: 44), LCDR1 having the amino acid sequence of TGTSSDIGAYDYVS (SEQ ID NO: 45), LCDR2 having the amino acid sequence of DATKRPS (SEQ ID NO: 46), LCDR3 having the amino acid sequence of CSYAGDYTPGVV (SEQ ID NO: 47); or HCDR1 having the amino acid sequence of RYSIN (SEQ ID NO: 48), HCDR2 having the amino acid sequence of GIIPIFGTANYAQRFQG (SEQ ID NO: 43), HCDR3 having the amino acid sequence of ENLDNSGTYYYYFSGWFDP (SEQ ID NO: 44), LCDR1 having the amino acid sequence of TGTSSDIDGYDFVS (SEQ ID NO: 49), LCDR2 having the amino acid sequence of DATKRPS (SEQ ID NO: 46), LCDR3 having the amino acid sequence of CSYAGDYTPGVV (SEQ ID NO: 47); or HCDR1 having the amino acid sequence of GYTIN (SEQ ID NO: 50), HCDR2 having the amino acid sequence of GIIPIFGTANYAQRFQG (SEQ ID NO: 43), HCDR3 having the amino acid sequence of ENLDNSGTYYYYFSGWFDP (SEQ ID NO: 44), LCDR1 having the amino acid sequence of TGTSSDLGGYDFVS (SEQ ID NO: 51), LCDR2 having the amino acid sequence of DATKRPS (SEQ ID NO: 46), LCDR3 having the amino acid sequence of CSYAGDYTPGVV (SEQ ID NO: 47); and wherein the antigen-binding fragment that binds to epitope III of rabies virus G protein comprises:

HCDR1 having the amino acid sequence of SYGMH (SEQ ID NO: 52), HCDR2 having the amino acid sequence of TISYDGSIKDYADSVKG (SEQ ID NO: 53), HCDR3 having the amino acid sequence of GDRTGNLDY (SEQ ID NO: 54), LCDR1 having the amino acid sequence of RASQNIRNALN (SEQ ID NO: 55), LCDR2 having the amino acid sequence of DASTRQS (SEQ ID NO: 56), LCDR3 having the amino acid sequence of QQNSEFPPT (SEQ ID NO: 57);

wherein the HCDR and LCDR amino acid sequences are defined according to Kabat.

2. The bispecific antibody of claim 1, wherein the amino acid sequence of the heavy chain variable region of the antigen-binding fragment that binds to epitope I of rabies virus G protein is shown in SEQ ID NO: 24, and the amino acid sequence of the light chain variable region of the antigen-binding fragment that binds to epitope I of rabies virus G protein is shown in SEQ ID NO: 25; or the amino acid sequence of the heavy chain variable region of the antigen-binding fragment that binds to epitope I of rabies virus G protein is shown in SEQ ID NO: 26, and the amino acid sequence of the light chain variable region of the antigen-binding fragment that binds to epitope I of rabies virus G protein is shown in SEQ ID NO: 27; or the amino acid sequence of the heavy chain variable region of the antigen-binding fragment that binds to epitope I of rabies virus G protein is shown in SEQ ID NO: 28, and the amino acid sequence of the light chain variable region of the antigen-binding fragment that binds to epitope I of rabies virus G protein is shown in SEQ ID NO: 29.

3. The bispecific antibody of claim 1, wherein the amino acid sequence of the heavy chain variable region of the antigen-binding fragment that binds to epitope III of rabies virus G protein is shown in SEQ ID NO: 1, and the amino acid sequence of the light chain variable region of the antigen-binding fragment that binds to epitope III of rabies virus G protein is shown in SEQ ID NO: 3.

4. The bispecific antibody of claim 1, wherein the forms of the two antigen-binding fragments are independently selected from a single chain antibody (scFv) or a Fab fragment.

5. The bispecific antibody of claim 4, wherein the antigen-binding fragment that binds to epitope I of rabies virus G protein is a single chain antibody (scFv) and the antigen-binding fragment that binds to epitope III of rabies virus G protein is a Fab fragment.

6. The bispecific antibody of claim 5, wherein the bispecific antibody comprises the amino acid sequence set forth in one of SEQ ID NO: 32, 33 and 34, and/or the bispecific antibody comprises the amino acid sequence set forth in SEQ ID NO: 30 and SEQ ID NO: 31.

7. A pharmaceutical composition comprising the bispecific antibody of claim 1 and a pharmaceutically acceptable excipient, diluent or carrier.

8. The pharmaceutical composition of claim 7, wherein the pharmaceutical composition is for use in the prevention or treatment of rabies.

9. A method of preventing or treating rabies comprising administering to a subject in need thereof the bispecific antibody of claim 1.

* * * * *

SEQUENCE LISTING

```
<160> NUMBER OF SEQ ID NOS: 64

<210> SEQ ID NO 1
<211> LENGTH: 118
<212> TYPE: PRT
<213> ORGANISM: Artificial Sequence
<220> FEATURE:
<223> OTHER INFORMATION: Synthetic

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Gly Ser Tyr
            20                  25                  30

Gly Met His Trp Val Arg Gln Ala Pro Gly Lys Gly Leu Glu Trp Val
        35                  40                  45

Ala Thr Ile Ser Tyr Asp Gly Ser Ile Lys Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Arg Thr Gly Asn Leu Asp Tyr Trp Gly Gln Gly Thr
            100                 105                 110

Leu Val Thr Val Ser Ser
```

<210> SEQ ID NO 2
<211> LENGTH: 127
<212> TYPE: PRT
<213> ORGANISM: Artificial Sequence
<220> FEATURE:
<223> OTHER INFORMATION: Synthetic

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Tyr Ser Arg Tyr
            20                  25                  30

Thr Leu Asn Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Arg Phe
    50                  55                  60

Gln Gly Arg Leu Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Phe Cys
                85                  90                  95

Ala Arg Glu Asn Leu Asp Asn Ser Gly Thr Tyr Tyr Tyr Phe Ser Gly
            100                 105                 110

Trp Phe Asp Pro Trp Gly Gln Gly Thr Leu Val Thr Val Ser Ser
        115                 120                 125

<210> SEQ ID NO 3
<211> LENGTH: 107
<212> TYPE: PRT
<213> ORGANISM: Artificial Sequence
<220> FEATURE:
<223> OTHER INFORMATION: Synthetic

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Arg Asn Ala
            20                  25                  30

Leu Asn Trp Tyr Gln Gln Lys Pro Gly Lys Ala Pro Lys Leu Leu Ile
        35                  40                  45

Tyr Asp Ala Ser Thr Arg Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Ser Glu Phe Pro Pro
                85                  90                  95

Thr Phe Gly Gln Gly Thr Lys Val Glu Ile Lys
            100                 105

<210> SEQ ID NO 4
<211> LENGTH: 112
<212> TYPE: PRT
<213> ORGANISM: Artificial Sequence
<220> FEATURE:
<223> OTHER INFORMATION: Synthetic

<400> SEQUENCE: 4

Gln Ser Ala Leu Thr Gln Pro Arg Ser Val Ser Gly Ser Pro Gly Gln
1               5                   10                  15

```
Ser Val Thr Ile Ser Cys Thr Gly Thr Ser Ser Asp Ile Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Ala Thr Lys Arg Pro Ser Gly Val Pro Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Asp
                85                  90                  95

Tyr Thr Pro Gly Val Val Phe Gly Gly Gly Thr Lys Leu Thr Val Leu
                100                 105                 110
```

<210> SEQ ID NO 5
<211> LENGTH: 330
<212> TYPE: PRT
<213> ORGANISM: Homo sapiens

<400> SEQUENCE: 5

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
                275                 280                 285
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 6
<211> LENGTH: 107
<212> TYPE: PRT
<213> ORGANISM: Homo sapiens

<400> SEQUENCE: 6

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 7
<211> LENGTH: 106
<212> TYPE: PRT
<213> ORGANISM: Homo sapiens

<400> SEQUENCE: 7

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 8
<211> LENGTH: 240
<212> TYPE: PRT
<213> ORGANISM: Artificial Sequence
<220> FEATURE:
<223> OTHER INFORMATION: Synthetic

<400> SEQUENCE: 8
```

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Gly Ser Tyr
            20                  25                  30

Gly Met His Trp Val Arg Gln Ala Pro Gly Lys Gly Leu Glu Trp Val
        35                  40                  45

Ala Thr Ile Ser Tyr Asp Gly Ser Ile Lys Tyr Ala Asp Ser Val
50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Arg Thr Gly Asn Leu Asp Tyr Trp Gly Gln Gly Thr
            100                 105                 110

Leu Val Thr Val Ser Ser Gly Gly Gly Gly Ser Gly Gly Gly Gly Ser
            115                 120                 125

Gly Gly Gly Gly Ser Asp Ile Gln Met Thr Gln Ser Pro Ser Ser Leu
        130                 135                 140

Ser Ala Ser Val Gly Asp Arg Val Thr Ile Thr Cys Arg Ala Ser Gln
145                 150                 155                 160

Asn Ile Arg Asn Ala Leu Asn Trp Tyr Gln Gln Lys Pro Gly Lys Ala
                165                 170                 175

Pro Lys Leu Leu Ile Tyr Asp Ala Ser Thr Arg Gln Ser Gly Val Pro
            180                 185                 190

Ser Arg Phe Ser Gly Ser Gly Ser Gly Thr Asp Phe Thr Leu Thr Ile
            195                 200                 205

Ser Ser Leu Gln Pro Glu Asp Phe Ala Thr Tyr Tyr Cys Gln Gln Asn
210                 215                 220

Ser Glu Phe Pro Pro Thr Phe Gly Gln Gly Thr Lys Val Glu Ile Lys
225                 230                 235                 240

<210> SEQ ID NO 9
<211> LENGTH: 254
<212> TYPE: PRT
<213> ORGANISM: Artificial Sequence
<220> FEATURE:
<223> OTHER INFORMATION: Synthetic

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Tyr Ser Arg Tyr
            20                  25                  30

Thr Leu Asn Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Arg Phe
50                  55                  60

Gln Gly Arg Leu Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Phe Cys
                85                  90                  95

Ala Arg Glu Asn Leu Asp Asn Ser Gly Thr Tyr Tyr Tyr Phe Ser Gly
            100                 105                 110

Trp Phe Asp Pro Trp Gly Gln Gly Thr Leu Val Thr Val Ser Ser Gly
            115                 120                 125
```

Gly Gly Gly Ser Gly Gly Gly Ser Gly Gly Gly Ser Gln Ser
        130             135             140

Ala Leu Thr Gln Pro Arg Ser Val Ser Gly Ser Pro Gly Gln Ser Val
145                 150                 155                 160

Thr Ile Ser Cys Thr Gly Thr Ser Ser Asp Ile Gly Gly Tyr Asn Tyr
                165                 170                 175

Val Ser Trp Tyr Gln Gln His Pro Gly Lys Ala Pro Lys Leu Met Ile
            180                 185                 190

Tyr Asp Ala Thr Lys Arg Pro Ser Gly Val Pro Asp Arg Phe Ser Gly
        195                 200                 205

Ser Lys Ser Gly Asn Thr Ala Ser Leu Thr Ile Ser Gly Leu Gln Ala
210                 215                 220

Glu Asp Glu Ala Asp Tyr Tyr Cys Cys Ser Tyr Ala Gly Asp Tyr Thr
225                 230                 235                 240

Pro Gly Val Val Phe Gly Gly Thr Lys Leu Thr Val Leu
                245                 250

<210> SEQ ID NO 10
<211> LENGTH: 232
<212> TYPE: PRT
<213> ORGANISM: Homo sapiens

<400> SEQUENCE: 10

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 11

<211> LENGTH: 232
<212> TYPE: PRT
<213> ORGANISM: Mus musculus

<400> SEQUENCE: 11

Pro Arg Gly Pro Thr Ile Lys Pro Cys Pro Pro Cys Lys Cys Pro Ala
1               5                   10                  15

Pro Asn Leu Leu Gly Gly Pro Ser Val Phe Ile Phe Pro Pro Lys Ile
            20                  25                  30

Lys Asp Val Leu Met Ile Ser Leu Ser Pro Ile Val Thr Cys Val Val
        35                  40                  45

Val Asp Val Ser Glu Asp Asp Pro Asp Val Gln Ile Ser Trp Phe Val
50                  55                  60

Asn Asn Val Glu Val His Thr Ala Gln Thr Gln Thr His Arg Glu Asp
65                  70                  75                  80

Tyr Asn Ser Thr Leu Arg Val Val Ser Ala Leu Pro Ile Gln His Gln
                85                  90                  95

Asp Trp Met Ser Gly Lys Glu Phe Lys Cys Lys Val Asn Asn Lys Asp
            100                 105                 110

Leu Pro Ala Pro Ile Glu Arg Thr Ile Ser Lys Pro Lys Gly Ser Val
        115                 120                 125

Arg Ala Pro Gln Val Tyr Val Leu Pro Pro Glu Glu Glu Met Thr
130                 135                 140

Lys Lys Gln Val Thr Leu Thr Cys Met Val Thr Asp Phe Met Pro Glu
145                 150                 155                 160

Asp Ile Tyr Val Glu Trp Thr Asn Asn Gly Lys Thr Glu Leu Asn Tyr
                165                 170                 175

Lys Asn Thr Glu Pro Val Leu Asp Ser Asp Gly Ser Tyr Phe Met Tyr
            180                 185                 190

Ser Lys Leu Arg Val Glu Lys Lys Asn Trp Val Glu Arg Asn Ser Tyr
        195                 200                 205

Ser Cys Ser Val Val His Glu Gly Leu His Asn His His Thr Thr Lys
    210                 215                 220

Ser Phe Ser Arg Thr Pro Gly Lys
225                 230

<210> SEQ ID NO 12
<211> LENGTH: 127
<212> TYPE: PRT
<213> ORGANISM: Artificial Sequence
<220> FEATURE:
<223> OTHER INFORMATION: Synthetic

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Arg Tyr
            20                  25                  30

Thr Val Asn Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Arg Phe
    50                  55                  60

Gln Gly Arg Leu Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Phe Cys
                85                  90                  95

Ala Arg Glu Asn Leu Asp Asn Ser Gly Thr Tyr Tyr Phe Ser Gly
            100                 105                 110

Trp Phe Asp Pro Trp Gly Gln Gly Thr Leu Val Thr Val Ser Ser
        115                 120                 125

<210> SEQ ID NO 13
<211> LENGTH: 119
<212> TYPE: PRT
<213> ORGANISM: Artificial Sequence
<220> FEATURE:
<223> OTHER INFORMATION: Synthetic

<400> SEQUENCE: 13

Glu Val Gln Leu Val Gln Ser Gly Gly Gly Ala Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Leu Tyr Asp Gly Ser Asp Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ala Val Ala Gly Thr His Phe Asp Tyr Trp Gly Gln Gly
            100                 105                 110

Thr Leu Val Thr Val Ser Ser
        115

<210> SEQ ID NO 14
<211> LENGTH: 330
<212> TYPE: PRT
<213> ORGANISM: Mus musculus

<400> SEQUENCE: 14

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg

```
                165                 170                 175
Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 15
<211> LENGTH: 112
<212> TYPE: PRT
<213> ORGANISM: Artificial Sequence
<220> FEATURE:
<223> OTHER INFORMATION: Synthetic

<400> SEQUENCE: 15

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Ile Gly Gly Tyr
            20                  25                  30

Asn Phe Val Ser Trp Tyr Gln Gln His Pro Gly Lys Ala Pro Lys Leu
        35                  40                  45

Met Ile Tyr Asp Ala Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Asp
                85                  90                  95

Tyr Thr Pro Gly Val Val Phe Gly Gly Gly Thr Lys Leu Thr Val Leu
            100                 105                 110

<210> SEQ ID NO 16
<211> LENGTH: 107
<212> TYPE: PRT
<213> ORGANISM: Artificial Sequence
<220> FEATURE:
<223> OTHER INFORMATION: Synthetic

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30
```

```
Leu Gly Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Pro
                 85                  90                  95

Thr Phe Gly Gly Gly Thr Lys Val Glu Ile Lys
            100                 105

<210> SEQ ID NO 17
<211> LENGTH: 106
<212> TYPE: PRT
<213> ORGANISM: Mus musculus

<400> SEQUENCE: 17

Gly Gln Pro Lys Ser Ser Pro Ser Val Thr Leu Phe Pro Pro Ser Ser
 1               5                  10                  15

Glu Glu Leu Glu Thr Asn Lys Ala Thr Leu Val Cys Thr Ile Thr Asp
             20                  25                  30

Phe Tyr Pro Gly Val Val Thr Val Asp Trp Lys Val Asp Gly Thr Pro
             35                  40                  45

Val Thr Gln Gly Met Glu Thr Thr Gln Pro Ser Lys Gln Ser Asn Asn
 50                  55                  60

Lys Tyr Met Ala Ser Ser Tyr Leu Thr Leu Thr Ala Arg Ala Trp Glu
 65                  70                  75                  80

Arg His Ser Ser Tyr Ser Cys Gln Val Thr His Glu Gly His Thr Val
                 85                  90                  95

Glu Lys Ser Leu Ser Arg Ala Asp Cys Ser
            100                 105

<210> SEQ ID NO 18
<211> LENGTH: 107
<212> TYPE: PRT
<213> ORGANISM: Mus musculus

<400> SEQUENCE: 18

Arg Ala Asp Ala Ala Pro Thr Val Ser Ile Phe Pro Pro Ser Ser Glu
 1               5                  10                  15

Gln Leu Thr Ser Gly Gly Ala Ser Val Val Cys Phe Leu Asn Asn Phe
             20                  25                  30

Tyr Pro Lys Asp Ile Asn Val Lys Trp Lys Ile Asp Gly Ser Glu Arg
             35                  40                  45

Gln Asn Gly Val Leu Asn Ser Trp Thr Asp Gln Asp Ser Lys Asp Ser
 50                  55                  60

Thr Tyr Ser Met Ser Ser Thr Leu Thr Leu Thr Lys Asp Glu Tyr Glu
 65                  70                  75                  80

Arg His Asn Ser Tyr Thr Cys Glu Ala Thr His Lys Thr Ser Thr Ser
                 85                  90                  95

Pro Ile Val Lys Ser Phe Asn Arg Asn Glu Cys
            100                 105

<210> SEQ ID NO 19
<211> LENGTH: 232
<212> TYPE: PRT
<213> ORGANISM: Artificial Sequence
<220> FEATURE:
```

<223> OTHER INFORMATION: Synthetic

<400> SEQUENCE: 19

| Glu | Pro | Lys | Ser | Cys | Asp | Lys | Thr | His | Thr | Cys | Pro | Pro | Cys | Pro | Ala |
|---|---|---|---|---|---|---|---|---|---|---|---|---|---|---|---|
| 1 | | | | 5 | | | | | 10 | | | | | 15 | |

| Pro | Glu | Leu | Leu | Gly | Gly | Pro | Ser | Val | Phe | Leu | Phe | Pro | Pro | Lys | Pro |
|---|---|---|---|---|---|---|---|---|---|---|---|---|---|---|---|
| | | | 20 | | | | | 25 | | | | | 30 | | |

| Lys | Asp | Thr | Leu | Met | Ile | Ser | Arg | Thr | Pro | Glu | Val | Thr | Cys | Val | Val |
|---|---|---|---|---|---|---|---|---|---|---|---|---|---|---|---|
| | | 35 | | | | | 40 | | | | | 45 | | | |

| Val | Asp | Val | Ser | His | Glu | Asp | Pro | Glu | Val | Lys | Phe | Asn | Trp | Tyr | Val |
|---|---|---|---|---|---|---|---|---|---|---|---|---|---|---|---|
| 50 | | | | | 55 | | | | | 60 | | | | | |

| Asp | Gly | Val | Glu | Val | His | Asn | Ala | Lys | Thr | Lys | Pro | Arg | Glu | Glu | Gln |
|---|---|---|---|---|---|---|---|---|---|---|---|---|---|---|---|
| 65 | | | | | 70 | | | | | 75 | | | | | 80 |

| Tyr | Asn | Ser | Thr | Tyr | Arg | Val | Val | Ser | Val | Leu | Thr | Val | Leu | His | Gln |
|---|---|---|---|---|---|---|---|---|---|---|---|---|---|---|---|
| | | | | 85 | | | | | 90 | | | | | 95 | |

| Asp | Trp | Leu | Asn | Gly | Lys | Glu | Tyr | Lys | Cys | Lys | Val | Ser | Asn | Lys | Ala |
|---|---|---|---|---|---|---|---|---|---|---|---|---|---|---|---|
| | | | 100 | | | | | 105 | | | | | 110 | | |

| Leu | Pro | Ala | Pro | Ile | Glu | Lys | Thr | Ile | Ser | Lys | Ala | Lys | Gly | Gln | Pro |
|---|---|---|---|---|---|---|---|---|---|---|---|---|---|---|---|
| | | 115 | | | | | 120 | | | | | 125 | | | |

| Arg | Glu | Pro | Gln | Val | Tyr | Thr | Leu | Pro | Pro | Cys | Arg | Glu | Glu | Met | Thr |
|---|---|---|---|---|---|---|---|---|---|---|---|---|---|---|---|
| 130 | | | | | 135 | | | | | 140 | | | | | |

| Lys | Asn | Gln | Val | Ser | Leu | Trp | Cys | Leu | Val | Lys | Gly | Phe | Tyr | Pro | Ser |
|---|---|---|---|---|---|---|---|---|---|---|---|---|---|---|---|
| 145 | | | | | 150 | | | | | 155 | | | | | 160 |

| Asp | Ile | Ala | Val | Glu | Trp | Glu | Ser | Asn | Gly | Gln | Pro | Glu | Asn | Asn | Tyr |
|---|---|---|---|---|---|---|---|---|---|---|---|---|---|---|---|
| | | | | 165 | | | | | 170 | | | | | 175 | |

| Lys | Thr | Thr | Pro | Pro | Val | Leu | Asp | Ser | Asp | Gly | Ser | Phe | Phe | Leu | Tyr |
|---|---|---|---|---|---|---|---|---|---|---|---|---|---|---|---|
| | | | 180 | | | | | 185 | | | | | 190 | | |

| Ser | Lys | Leu | Thr | Val | Asp | Lys | Ser | Arg | Trp | Gln | Gln | Gly | Asn | Val | Phe |
|---|---|---|---|---|---|---|---|---|---|---|---|---|---|---|---|
| | | | 195 | | | | | 200 | | | | | 205 | | |

| Ser | Cys | Ser | Val | Met | His | Glu | Ala | Leu | His | Asn | His | Tyr | Thr | Gln | Lys |
|---|---|---|---|---|---|---|---|---|---|---|---|---|---|---|---|
| | 210 | | | | | 215 | | | | | 220 | | | | |

| Ser | Leu | Ser | Leu | Ser | Pro | Gly | Lys |
|---|---|---|---|---|---|---|---|
| 225 | | | | | 230 | | |

<210> SEQ ID NO 20
<211> LENGTH: 232
<212> TYPE: PRT
<213> ORGANISM: Artificial Sequence
<220> FEATURE:
<223> OTHER INFORMATION: Synthetic

<400> SEQUENCE: 20

| Glu | Pro | Lys | Ser | Ser | Asp | Lys | Thr | His | Thr | Cys | Pro | Pro | Cys | Pro | Ala |
|---|---|---|---|---|---|---|---|---|---|---|---|---|---|---|---|
| 1 | | | | 5 | | | | | 10 | | | | | 15 | |

| Pro | Glu | Leu | Leu | Gly | Gly | Pro | Ser | Val | Phe | Leu | Phe | Pro | Pro | Lys | Pro |
|---|---|---|---|---|---|---|---|---|---|---|---|---|---|---|---|
| | | | 20 | | | | | 25 | | | | | 30 | | |

| Lys | Asp | Thr | Leu | Met | Ile | Ser | Arg | Thr | Pro | Glu | Val | Thr | Cys | Val | Val |
|---|---|---|---|---|---|---|---|---|---|---|---|---|---|---|---|
| | | 35 | | | | | 40 | | | | | 45 | | | |

| Val | Asp | Val | Ser | His | Glu | Asp | Pro | Glu | Val | Lys | Phe | Asn | Trp | Tyr | Val |
|---|---|---|---|---|---|---|---|---|---|---|---|---|---|---|---|
| 50 | | | | | 55 | | | | | 60 | | | | | |

| Asp | Gly | Val | Glu | Val | His | Asn | Ala | Lys | Thr | Lys | Pro | Arg | Glu | Glu | Gln |
|---|---|---|---|---|---|---|---|---|---|---|---|---|---|---|---|
| 65 | | | | | 70 | | | | | 75 | | | | | 80 |

| Tyr | Asn | Ser | Thr | Tyr | Arg | Val | Val | Ser | Val | Leu | Thr | Val | Leu | His | Gln |
|---|---|---|---|---|---|---|---|---|---|---|---|---|---|---|---|
| | | | | 85 | | | | | 90 | | | | | 95 | |

| Asp | Trp | Leu | Asn | Gly | Lys | Glu | Tyr | Lys | Cys | Lys | Val | Ser | Asn | Lys | Ala |
|---|---|---|---|---|---|---|---|---|---|---|---|---|---|---|---|
| | | | 100 | | | | | 105 | | | | | 110 | | |

```
Leu Pro Ala Pro Ile Glu Lys Thr Ile Ser Lys Ala Lys Gly Gln Pro
            115                 120                 125

Arg Glu Pro Gln Val Cys Thr Leu Pro Pro Ser Arg Glu Glu Met Thr
        130                 135                 140

Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Val
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 21
<211> LENGTH: 254
<212> TYPE: PRT
<213> ORGANISM: Artificial Sequence
<220> FEATURE:
<223> OTHER INFORMATION: Synthetic

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Tyr Ser Arg Tyr
            20                  25                  30

Thr Ile Asn Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Arg Phe
    50                  55                  60

Gln Gly Arg Leu Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Phe Cys
                85                  90                  95

Ala Arg Glu Asn Leu Asp Asn Ser Gly Thr Tyr Tyr Tyr Phe Ser Gly
            100                 105                 110

Trp Phe Asp Pro Trp Gly Gln Gly Thr Leu Val Thr Val Ser Ser Gly
        115                 120                 125

Gly Gly Gly Ser Gly Gly Gly Gly Ser Gly Gly Gly Gly Ser Gln Ser
    130                 135                 140

Ala Leu Thr Gln Pro Arg Ser Val Ser Gly Ser Pro Gly Gln Ser Val
145                 150                 155                 160

Thr Ile Ser Cys Thr Gly Thr Ser Ser Asp Ile Gly Ala Tyr Asp Tyr
                165                 170                 175

Val Ser Trp Tyr Gln Gln His Pro Gly Lys Ala Pro Lys Leu Met Ile
            180                 185                 190

Tyr Asp Ala Thr Lys Arg Pro Ser Gly Val Pro Asp Arg Phe Ser Gly
        195                 200                 205

Ser Lys Ser Gly Asn Thr Ala Ser Leu Thr Ile Ser Gly Leu Gln Ala
    210                 215                 220

Glu Asp Glu Ala Asp Tyr Tyr Cys Cys Ser Tyr Ala Gly Asp Tyr Thr
225                 230                 235                 240
```

```
Pro Gly Val Val Phe Gly Gly Gly Thr Lys Leu Thr Val Leu
            245                 250
```

<210> SEQ ID NO 22
<211> LENGTH: 254
<212> TYPE: PRT
<213> ORGANISM: Artificial Sequence
<220> FEATURE:
<223> OTHER INFORMATION: Synthetic

<400> SEQUENCE: 22

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Tyr Ser Arg Tyr
            20                  25                  30

Ser Ile Asn Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Arg Phe
    50                  55                  60

Gln Gly Arg Leu Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Phe Cys
                85                  90                  95

Ala Arg Glu Asn Leu Asp Asn Ser Gly Thr Tyr Tyr Tyr Phe Ser Gly
            100                 105                 110

Trp Phe Asp Pro Trp Gly Gln Gly Thr Leu Val Thr Val Ser Ser Gly
        115                 120                 125

Gly Gly Gly Ser Gly Gly Gly Gly Ser Gly Gly Gly Gly Ser Gln Ser
    130                 135                 140

Ala Leu Thr Gln Pro Arg Ser Val Ser Gly Ser Pro Gly Gln Ser Val
145                 150                 155                 160

Thr Ile Ser Cys Thr Gly Thr Ser Ser Asp Ile Asp Gly Tyr Asp Phe
                165                 170                 175

Val Ser Trp Tyr Gln Gln His Pro Gly Lys Ala Pro Lys Leu Met Ile
            180                 185                 190

Tyr Asp Ala Thr Lys Arg Pro Ser Gly Val Pro Asp Arg Phe Ser Gly
        195                 200                 205

Ser Lys Ser Gly Asn Thr Ala Ser Leu Thr Ile Ser Gly Leu Gln Ala
    210                 215                 220

Glu Asp Glu Ala Asp Tyr Tyr Cys Cys Ser Tyr Ala Gly Asp Tyr Thr
225                 230                 235                 240

Pro Gly Val Val Phe Gly Gly Gly Thr Lys Leu Thr Val Leu
                245                 250
```

<210> SEQ ID NO 23
<211> LENGTH: 254
<212> TYPE: PRT
<213> ORGANISM: Artificial Sequence
<220> FEATURE:
<223> OTHER INFORMATION: Synthetic

<400> SEQUENCE: 23

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Tyr Ser Gly Tyr
            20                  25                  30

Thr Ile Asn Trp Val Arg Gln Ala Pro Gly Gln Gly Leu Glu Trp Met
```

```
            35                  40                  45
Gly Gly Ile Ile Pro Ile Phe Gly Thr Ala Asn Tyr Ala Gln Arg Phe
 50                  55                  60

Gln Gly Arg Leu Thr Ile Thr Ala Asp Glu Ser Thr Ser Thr Ala Tyr
 65                  70                  75                  80

Met Glu Leu Ser Ser Leu Arg Ser Asp Asp Thr Ala Val Tyr Phe Cys
                 85                  90                  95

Ala Arg Glu Asn Leu Asp Asn Ser Gly Thr Tyr Tyr Tyr Phe Ser Gly
                100                 105                 110

Trp Phe Asp Pro Trp Gly Gln Gly Thr Leu Val Thr Val Ser Ser Gly
            115                 120                 125

Gly Gly Gly Ser Gly Gly Gly Gly Ser Gly Gly Gly Gly Ser Gln Ser
    130                 135                 140

Ala Leu Thr Gln Pro Arg Ser Val Ser Gly Ser Pro Gly Gln Ser Val
145                 150                 155                 160

Thr Ile Ser Cys Thr Gly Thr Ser Ser Asp Leu Gly Gly Tyr Asp Phe
                165                 170                 175

Val Ser Trp Tyr Gln Gln His Pro Gly Lys Ala Pro Lys Leu Met Ile
            180                 185                 190

Tyr Asp Ala Thr Lys Arg Pro Ser Gly Val Pro Asp Arg Phe Ser Gly
        195                 200                 205

Ser Lys Ser Gly Asn Thr Ala Ser Leu Thr Ile Ser Gly Leu Gln Ala
    210                 215                 220

Glu Asp Glu Ala Asp Tyr Tyr Cys Cys Ser Tyr Ala Gly Asp Tyr Thr
225                 230                 235                 240

Pro Gly Val Val Phe Gly Gly Thr Lys Leu Thr Val Leu
                245                 250

<210> SEQ ID NO 24
<211> LENGTH: 127
<212> TYPE: PRT
<213> ORGANISM: Artificial Sequence
<220> FEATURE:
<223> OTHER INFORMATION: Synthetic

<400> SEQUENCE: 24

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Tyr Ser Arg Tyr
                 20                  25                  30

Thr Ile Asn Trp Val Arg Gln Ala Pro Gly Gln Gly Leu Glu Trp Met
             35                  40                  45

Gly Gly Ile Ile Pro Ile Phe Gly Thr Ala Asn Tyr Ala Gln Arg Phe
 50                  55                  60

Gln Gly Arg Leu Thr Ile Thr Ala Asp Glu Ser Thr Ser Thr Ala Tyr
 65                  70                  75                  80

Met Glu Leu Ser Ser Leu Arg Ser Asp Asp Thr Ala Val Tyr Phe Cys
                 85                  90                  95

Ala Arg Glu Asn Leu Asp Asn Ser Gly Thr Tyr Tyr Tyr Phe Ser Gly
                100                 105                 110

Trp Phe Asp Pro Trp Gly Gln Gly Thr Leu Val Thr Val Ser Ser
            115                 120                 125

<210> SEQ ID NO 25
<211> LENGTH: 112
<212> TYPE: PRT
```

```
<213> ORGANISM: Artificial Sequence
<220> FEATURE:
<223> OTHER INFORMATION: Synthetic

<400> SEQUENCE: 25

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Ile Gly Ala Tyr
            20                  25                  30

Asp Tyr Val Ser Trp Tyr Gln Gln His Pro Gly Lys Ala Pro Lys Leu
        35                  40                  45

Met Ile Tyr Asp Ala Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Asp
                85                  90                  95

Tyr Thr Pro Gly Val Val Phe Gly Gly Gly Thr Lys Leu Thr Val Leu
            100                 105                 110

<210> SEQ ID NO 26
<211> LENGTH: 127
<212> TYPE: PRT
<213> ORGANISM: Artificial Sequence
<220> FEATURE:
<223> OTHER INFORMATION: Synthetic

<400> SEQUENCE: 26

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Tyr Ser Arg Tyr
            20                  25                  30

Ser Ile Asn Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Arg Phe
    50                  55                  60

Gln Gly Arg Leu Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Phe Cys
                85                  90                  95

Ala Arg Glu Asn Leu Asp Asn Ser Gly Thr Tyr Tyr Phe Ser Gly
            100                 105                 110

Trp Phe Asp Pro Trp Gly Gln Gly Thr Leu Val Thr Val Ser Ser
        115                 120                 125

<210> SEQ ID NO 27
<211> LENGTH: 112
<212> TYPE: PRT
<213> ORGANISM: Artificial Sequence
<220> FEATURE:
<223> OTHER INFORMATION: Synthetic

<400> SEQUENCE: 27

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Ile Asp Gly Tyr
            20                  25                  30

Asp Phe Val Ser Trp Tyr Gln Gln His Pro Gly Lys Ala Pro Lys Leu
        35                  40                  45
```

```
Met Ile Tyr Asp Ala Thr Lys Arg Pro Ser Gly Val Pro Asp Arg Phe
        50                   55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Asp
                85                  90                  95

Tyr Thr Pro Gly Val Val Phe Gly Gly Gly Thr Lys Leu Thr Val Leu
            100                 105                 110
```

<210> SEQ ID NO 28
<211> LENGTH: 127
<212> TYPE: PRT
<213> ORGANISM: Artificial Sequence
<220> FEATURE:
<223> OTHER INFORMATION: Synthetic

<400> SEQUENCE: 28

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Tyr Ser Gly Tyr
            20                  25                  30

Thr Ile Asn Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Arg Phe
    50                  55                  60

Gln Gly Arg Leu Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Phe Cys
                85                  90                  95

Ala Arg Glu Asn Leu Asp Asn Ser Gly Thr Tyr Tyr Tyr Phe Ser Gly
            100                 105                 110

Trp Phe Asp Pro Trp Gly Gln Gly Thr Leu Val Thr Val Ser Ser
        115                 120                 125
```

<210> SEQ ID NO 29
<211> LENGTH: 112
<212> TYPE: PRT
<213> ORGANISM: Artificial Sequence
<220> FEATURE:
<223> OTHER INFORMATION: Synthetic

<400> SEQUENCE: 29

```
Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Leu Gly Gly Tyr
            20                  25                  30

Asp Phe Val Ser Trp Tyr Gln Gln His Pro Gly Lys Ala Pro Lys Leu
        35                  40                  45

Met Ile Tyr Asp Ala Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Asp
                85                  90                  95

Tyr Thr Pro Gly Val Val Phe Gly Gly Gly Thr Lys Leu Thr Val Leu
            100                 105                 110
```

-continued

<210> SEQ ID NO 30
<211> LENGTH: 214
<212> TYPE: PRT
<213> ORGANISM: Homo sapiens

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Arg Asn Ala
            20                  25                  30

Leu Asn Trp Tyr Gln Gln Lys Pro Gly Lys Ala Pro Lys Leu Leu Ile
        35                  40                  45

Tyr Asp Ala Ser Thr Arg Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Ser Glu Phe Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 31
<211> LENGTH: 448
<212> TYPE: PRT
<213> ORGANISM: Artificial Sequence
<220> FEATURE:
<223> OTHER INFORMATION: Synthetic

<400> SEQUENCE: 31

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Gly Ser Tyr
            20                  25                  30

Gly Met His Trp Val Arg Gln Ala Pro Gly Lys Gly Leu Glu Trp Val
        35                  40                  45

Ala Thr Ile Ser Tyr Asp Gly Ser Ile Lys Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Arg Thr Gly Asn Leu Asp Tyr Trp Gly Gln Gly Thr
            100                 105                 110

```
Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Glu Glu Met Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 32
<211> LENGTH: 488
<212> TYPE: PRT
<213> ORGANISM: Artificial Sequence
<220> FEATURE:
<223> OTHER INFORMATION: Synthetic

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Tyr Ser Gly Tyr
            20                  25                  30
```

```
Thr Ile Asn Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Arg Phe
 50                  55                  60

Gln Gly Arg Leu Thr Ile Thr Ala Asp Glu Ser Thr Ser Thr Ala Tyr
 65                  70                  75                  80

Met Glu Leu Ser Ser Leu Arg Ser Asp Thr Ala Val Tyr Phe Cys
                 85                  90                  95

Ala Arg Glu Asn Leu Asp Asn Ser Gly Thr Tyr Tyr Phe Ser Gly
                 100                 105                 110

Trp Phe Asp Pro Trp Gly Gln Gly Thr Leu Val Thr Val Ser Ser Gly
             115                 120                 125

Gly Gly Gly Ser Gly Gly Gly Ser Gly Gly Gly Ser Gln Ser
 130                 135                 140

Ala Leu Thr Gln Pro Arg Ser Val Ser Gly Ser Pro Gly Gln Ser Val
145                 150                 155                 160

Thr Ile Ser Cys Thr Gly Thr Ser Ser Asp Leu Gly Gly Tyr Asp Phe
                 165                 170                 175

Val Ser Trp Tyr Gln Gln His Pro Gly Lys Ala Pro Lys Leu Met Ile
             180                 185                 190

Tyr Asp Ala Thr Lys Arg Pro Ser Gly Val Pro Asp Arg Phe Ser Gly
             195                 200                 205

Ser Lys Ser Gly Asn Thr Ala Ser Leu Thr Ile Ser Gly Leu Gln Ala
     210                 215                 220

Glu Asp Glu Ala Asp Tyr Tyr Cys Cys Ser Tyr Ala Gly Asp Tyr Thr
225                 230                 235                 240

Pro Gly Val Val Phe Gly Gly Gly Thr Lys Leu Thr Val Leu Ala Ser
                 245                 250                 255

Glu Pro Lys Ser Ser Asp Lys Thr His Thr Cys Pro Pro Cys Pro Ala
             260                 265                 270

Pro Glu Leu Leu Gly Gly Pro Ser Val Phe Leu Phe Pro Pro Lys Pro
     275                 280                 285

Lys Asp Thr Leu Met Ile Ser Arg Thr Pro Glu Val Thr Cys Val Val
290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                 325                 330                 335

Tyr Asn Ser Thr Tyr Arg Val Val Ser Val Leu Thr Val Leu His Gln
             340                 345                 350

Asp Trp Leu Asn Gly Lys Glu Tyr Lys Cys Lys Val Ser Asn Lys Ala
             355                 360                 365

Leu Pro Ala Pro Ile Glu Lys Thr Ile Ser Lys Ala Lys Gly Gln Pro
 370                 375                 380

Arg Glu Pro Gln Val Cys Thr Leu Pro Pro Ser Arg Glu Glu Met Thr
385                 390                 395                 400

Lys Asn Gln Val Ser Leu Ser Cys Ala Val Lys Gly Phe Tyr Pro Ser
                 405                 410                 415

Asp Ile Ala Val Glu Trp Glu Ser Asn Gly Gln Pro Glu Asn Asn Tyr
             420                 425                 430

Lys Thr Thr Pro Pro Val Leu Asp Ser Asp Gly Ser Phe Phe Leu Val
             435                 440                 445
```

```
Ser Lys Leu Thr Val Asp Lys Ser Arg Trp Gln Gln Gly Asn Val Phe
    450                 455                 460
Ser Cys Ser Val Met His Glu Ala Leu His Asn His Tyr Thr Gln Lys
465                 470                 475                 480
Ser Leu Ser Leu Ser Pro Gly Lys
                485

<210> SEQ ID NO 33
<211> LENGTH: 488
<212> TYPE: PRT
<213> ORGANISM: Artificial Sequence
<220> FEATURE:
<223> OTHER INFORMATION: Synthetic

<400> SEQUENCE: 33

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Tyr Ser Arg Tyr
            20                  25                  30
Thr Ile Asn Trp Val Arg Gln Ala Pro Gly Gln Gly Leu Glu Trp Met
        35                  40                  45
Gly Gly Ile Ile Pro Ile Phe Gly Thr Ala Asn Tyr Ala Gln Arg Phe
    50                  55                  60
Gln Gly Arg Leu Thr Ile Thr Ala Asp Glu Ser Thr Ser Thr Ala Tyr
65                  70                  75                  80
Met Glu Leu Ser Ser Leu Arg Ser Asp Asp Thr Ala Val Tyr Phe Cys
                85                  90                  95
Ala Arg Glu Asn Leu Asp Asn Ser Gly Thr Tyr Tyr Phe Ser Gly
            100                 105                 110
Trp Phe Asp Pro Trp Gly Gln Gly Thr Leu Val Thr Val Ser Ser Gly
        115                 120                 125
Gly Gly Gly Ser Gly Gly Gly Gly Ser Gly Gly Gly Gly Ser Gln Ser
    130                 135                 140
Ala Leu Thr Gln Pro Arg Ser Val Ser Gly Ser Pro Gly Gln Ser Val
145                 150                 155                 160
Thr Ile Ser Cys Thr Gly Thr Ser Ser Asp Ile Gly Ala Tyr Asp Tyr
                165                 170                 175
Val Ser Trp Tyr Gln Gln His Pro Gly Lys Ala Pro Lys Leu Met Ile
            180                 185                 190
Tyr Asp Ala Thr Lys Arg Pro Ser Gly Val Pro Asp Arg Phe Ser Gly
        195                 200                 205
Ser Lys Ser Gly Asn Thr Ala Ser Leu Thr Ile Ser Gly Leu Gln Ala
    210                 215                 220
Glu Asp Glu Ala Asp Tyr Tyr Cys Cys Ser Tyr Ala Gly Asp Tyr Thr
225                 230                 235                 240
Pro Gly Val Val Phe Gly Gly Gly Thr Lys Leu Thr Val Leu Ala Ser
                245                 250                 255
Glu Pro Lys Ser Ser Asp Lys Thr His Thr Cys Pro Pro Cys Pro Ala
            260                 265                 270
Pro Glu Leu Leu Gly Gly Pro Ser Val Phe Leu Phe Pro Pro Lys Pro
        275                 280                 285
Lys Asp Thr Leu Met Ile Ser Arg Thr Pro Glu Val Thr Cys Val Val
    290                 295                 300
Val Asp Val Ser His Glu Asp Pro Glu Val Lys Phe Asn Trp Tyr Val
305                 310                 315                 320
```

Asp Gly Val Glu Val His Asn Ala Lys Thr Lys Pro Arg Glu Glu Gln
            325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
            355                 360                 365

Leu Pro Ala Pro Ile Glu Lys Thr Ile Ser Lys Ala Lys Gly Gln Pro
        370                 375                 380

Arg Glu Pro Gln Val Cys Thr Leu Pro Pro Ser Arg Glu Glu Met Thr
385                 390                 395                 400

Lys Asn Gln Val Ser Leu Ser Cys Ala Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Val
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys
                485

<210> SEQ ID NO 34
<211> LENGTH: 488
<212> TYPE: PRT
<213> ORGANISM: Artificial Sequence
<220> FEATURE:
<223> OTHER INFORMATION: Synthetic

<400> SEQUENCE: 34

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Tyr Ser Arg Tyr
            20                  25                  30

Ser Ile Asn Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Arg Phe
    50                  55                  60

Gln Gly Arg Leu Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Phe Cys
                85                  90                  95

Ala Arg Glu Asn Leu Asp Asn Ser Gly Thr Tyr Tyr Tyr Phe Ser Gly
            100                 105                 110

Trp Phe Asp Pro Trp Gly Gln Gly Thr Leu Val Thr Val Ser Ser Gly
        115                 120                 125

Gly Gly Gly Ser Gly Gly Gly Gly Ser Gly Gly Gly Gly Ser Gln Ser
    130                 135                 140

Ala Leu Thr Gln Pro Arg Ser Val Ser Gly Ser Pro Gly Gln Ser Val
145                 150                 155                 160

Thr Ile Ser Cys Thr Gly Thr Ser Ser Asp Ile Asp Gly Tyr Asp Phe
                165                 170                 175

Val Ser Trp Tyr Gln Gln His Pro Gly Lys Ala Pro Lys Leu Met Ile
            180                 185                 190

-continued

```
Tyr Asp Ala Thr Lys Arg Pro Ser Gly Val Pro Asp Arg Phe Ser Gly
            195                 200                 205
Ser Lys Ser Gly Asn Thr Ala Ser Leu Thr Ile Ser Gly Leu Gln Ala
    210                 215                 220
Glu Asp Glu Ala Asp Tyr Tyr Cys Ser Tyr Ala Gly Asp Tyr Thr
225                 230                 235                 240
Pro Gly Val Val Phe Gly Gly Thr Lys Leu Thr Val Leu Ala Ser
                245                 250                 255
Glu Pro Lys Ser Ser Asp Lys Thr His Thr Cys Pro Pro Cys Pro Ala
            260                 265                 270
Pro Glu Leu Leu Gly Gly Pro Ser Val Phe Leu Phe Pro Pro Lys Pro
        275                 280                 285
Lys Asp Thr Leu Met Ile Ser Arg Thr Pro Glu Val Thr Cys Val Val
    290                 295                 300
Val Asp Val Ser His Glu Asp Pro Glu Val Lys Phe Asn Trp Tyr Val
305                 310                 315                 320
Asp Gly Val Glu Val His Asn Ala Lys Thr Lys Pro Arg Glu Glu Gln
                325                 330                 335
Tyr Asn Ser Thr Tyr Arg Val Val Ser Val Leu Thr Val Leu His Gln
            340                 345                 350
Asp Trp Leu Asn Gly Lys Glu Tyr Lys Cys Lys Val Ser Asn Lys Ala
        355                 360                 365
Leu Pro Ala Pro Ile Glu Lys Thr Ile Ser Lys Ala Lys Gly Gln Pro
    370                 375                 380
Arg Glu Pro Gln Val Cys Thr Leu Pro Pro Ser Arg Glu Glu Met Thr
385                 390                 395                 400
Lys Asn Gln Val Ser Leu Ser Cys Ala Val Lys Gly Phe Tyr Pro Ser
                405                 410                 415
Asp Ile Ala Val Glu Trp Glu Ser Asn Gly Gln Pro Glu Asn Asn Tyr
            420                 425                 430
Lys Thr Thr Pro Pro Val Leu Asp Ser Asp Gly Ser Phe Phe Leu Val
        435                 440                 445
Ser Lys Leu Thr Val Asp Lys Ser Arg Trp Gln Gln Gly Asn Val Phe
    450                 455                 460
Ser Cys Ser Val Met His Glu Ala Leu His Asn His Tyr Thr Gln Lys
465                 470                 475                 480
Ser Leu Ser Leu Ser Pro Gly Lys
                485

<210> SEQ ID NO 35
<211> LENGTH: 440
<212> TYPE: PRT
<213> ORGANISM: Rabies virus

<400> SEQUENCE: 35

Lys Phe Pro Ile Tyr Thr Ile Pro Asp Lys Leu Gly Pro Trp Ser Pro
1               5                   10                  15
Ile Asp Ile His His Leu Ser Cys Pro Asn Asn Leu Val Val Glu Asp
            20                  25                  30
Glu Gly Cys Thr Asn Leu Ser Glu Phe Ser Tyr Met Glu Leu Lys Val
        35                  40                  45
Gly Tyr Ile Ser Ala Ile Lys Val Asn Gly Phe Thr Cys Thr Gly Val
    50                  55                  60
Val Thr Glu Ala Glu Thr Tyr Thr Asn Phe Val Gly Tyr Val Thr Thr
65                  70                  75                  80
```

```
Thr Phe Lys Arg Lys His Phe Arg Pro Thr Pro Asp Ala Cys Arg Ala
                85                  90                  95

Ala Tyr Asn Trp Lys Met Ala Gly Asp Pro Arg Tyr Glu Glu Ser Leu
            100                 105                 110

His Asn Pro Tyr Pro Asp Tyr His Trp Leu Arg Thr Val Arg Thr Thr
        115                 120                 125

Lys Glu Ser Leu Ile Ile Ile Ser Pro Ser Val Thr Asp Leu Asp Pro
    130                 135                 140

Tyr Asp Lys Ser Leu His Ser Arg Val Phe Pro Gly Gly Lys Cys Ser
145                 150                 155                 160

Gly Ile Thr Val Ser Ser Thr Tyr Cys Ser Thr Asn His Asp Tyr Thr
                165                 170                 175

Ile Trp Met Pro Glu Asn Pro Arg Pro Arg Thr Pro Cys Asp Ile Phe
            180                 185                 190

Thr Asn Ser Arg Gly Lys Arg Ala Ser Lys Gly Asn Lys Thr Cys Gly
        195                 200                 205

Phe Val Asp Glu Arg Gly Leu Tyr Lys Ser Leu Lys Gly Ala Cys Arg
    210                 215                 220

Leu Lys Leu Cys Gly Val Leu Gly Leu Arg Leu Met Asp Gly Thr Trp
225                 230                 235                 240

Val Ala Met Gln Thr Ser Asp Glu Thr Lys Trp Cys Pro Pro Asp Gln
                245                 250                 255

Leu Val Asn Leu His Asp Phe Arg Ser Asp Glu Ile Glu His Leu Val
            260                 265                 270

Val Glu Glu Leu Val Lys Lys Arg Glu Glu Cys Leu Asp Ala Leu Glu
        275                 280                 285

Ser Ile Met Thr Thr Lys Ser Val Ser Phe Arg Arg Leu Ser His Leu
    290                 295                 300

Arg Lys Leu Val Pro Gly Phe Gly Lys Ala Tyr Thr Ile Phe Asn Lys
305                 310                 315                 320

Thr Leu Met Glu Ala Asp Ala His Tyr Lys Ser Val Arg Thr Trp Asn
                325                 330                 335

Glu Ile Ile Pro Ser Lys Gly Cys Leu Lys Val Gly Gly Arg Cys His
            340                 345                 350

Pro His Val Asn Gly Val Phe Phe Asn Gly Ile Ile Leu Gly Pro Asp
        355                 360                 365

Gly His Val Leu Ile Pro Glu Met Gln Ser Ser Leu Leu Gln Gln His
    370                 375                 380

Met Glu Leu Leu Lys Ser Ser Val Ile Pro Leu Met His Pro Leu Ala
385                 390                 395                 400

Asp Pro Ser Thr Val Phe Lys Glu Gly Asp Glu Ala Glu Asp Phe Val
                405                 410                 415

Glu Val His Leu Pro Asp Val Tyr Lys Gln Ile Ser Gly Val Asp Leu
            420                 425                 430

Gly Leu Pro Asn Trp Gly Lys Tyr
        435                 440

<210> SEQ ID NO 36
<211> LENGTH: 440
<212> TYPE: PRT
<213> ORGANISM: Artificial Sequence
<220> FEATURE:
<223> OTHER INFORMATION: Synthetic

<400> SEQUENCE: 36
```

```
Lys Phe Pro Ile Tyr Thr Ile Pro Asp Lys Leu Gly Pro Trp Ser Pro
1               5                   10                  15

Ile Asp Ile His His Leu Ser Cys Pro Asn Asn Leu Val Val Glu Asp
                20                  25                  30

Glu Gly Cys Thr Asn Leu Ser Glu Phe Ser Tyr Met Glu Leu Lys Val
            35                  40                  45

Gly Tyr Ile Ser Ala Ile Lys Val Asn Gly Phe Thr Cys Thr Gly Val
        50                  55                  60

Val Thr Glu Ala Glu Thr Tyr Thr Asn Phe Val Gly Tyr Val Thr Thr
65                  70                  75                  80

Thr Phe Lys Arg Lys His Phe Arg Pro Thr Pro Asp Ala Cys Arg Ala
                85                  90                  95

Ala Tyr Asn Trp Lys Met Ala Gly Asp Pro Arg Tyr Glu Glu Ser Leu
            100                 105                 110

His Asn Pro Tyr Pro Asp Tyr His Trp Leu Arg Thr Val Arg Thr Thr
        115                 120                 125

Lys Glu Ser Leu Ile Ile Ile Ser Pro Ser Val Thr Asp Leu Asp Pro
    130                 135                 140

Tyr Asp Lys Ser Leu His Ser Arg Val Phe Pro Gly Gly Lys Cys Ser
145                 150                 155                 160

Gly Ile Thr Val Ser Ser Thr Tyr Cys Ser Thr Asn His Asp Tyr Thr
                165                 170                 175

Ile Trp Met Pro Glu Asn Pro Arg Pro Arg Thr Pro Cys Asp Ile Phe
            180                 185                 190

Thr Asn Ser Arg Gly Lys Arg Ala Ser Lys Gly Asn Lys Thr Cys Gly
        195                 200                 205

Phe Val Asp Glu Arg Gly Leu Tyr Lys Ser Leu Lys Gly Ala Cys Arg
    210                 215                 220

Leu Lys Leu Cys Glu Val Leu Gly Leu Arg Leu Met Asp Gly Thr Trp
225                 230                 235                 240

Val Ala Met Gln Thr Ser Asp Glu Thr Lys Trp Cys Pro Pro Asp Gln
                245                 250                 255

Leu Val Asn Leu His Asp Phe Arg Ser Asp Glu Ile Glu His Leu Val
            260                 265                 270

Val Glu Glu Leu Val Lys Lys Arg Glu Glu Cys Leu Asp Ala Leu Glu
        275                 280                 285

Ser Ile Met Thr Thr Lys Ser Val Ser Phe Arg Arg Leu Ser His Leu
    290                 295                 300

Arg Lys Leu Val Pro Gly Phe Gly Lys Ala Tyr Thr Ile Phe Asn Lys
305                 310                 315                 320

Thr Leu Met Glu Ala Asp Ala His Tyr Lys Ser Val Arg Thr Trp Asn
                325                 330                 335

Glu Ile Ile Pro Ser Lys Gly Cys Leu Lys Val Gly Gly Arg Cys His
            340                 345                 350

Pro His Val Asn Gly Val Phe Phe Asn Gly Ile Ile Leu Gly Pro Asp
        355                 360                 365

Gly His Val Leu Ile Pro Glu Met Gln Ser Ser Leu Leu Gln Gln His
    370                 375                 380

Met Glu Leu Leu Lys Ser Ser Val Ile Pro Leu Met His Pro Leu Ala
385                 390                 395                 400

Asp Pro Ser Thr Val Phe Lys Glu Gly Asp Glu Ala Glu Asp Phe Val
                405                 410                 415
```

Glu Val His Leu Pro Asp Val Tyr Lys Gln Ile Ser Gly Val Asp Leu
            420                 425                 430

Gly Leu Pro Asn Trp Gly Lys Tyr
        435                 440

<210> SEQ ID NO 37
<211> LENGTH: 440
<212> TYPE: PRT
<213> ORGANISM: Artificial Sequence
<220> FEATURE:
<223> OTHER INFORMATION: Synthetic

<400> SEQUENCE: 37

Lys Phe Pro Ile Tyr Thr Ile Pro Asp Lys Leu Gly Pro Trp Ser Pro
1               5                   10                  15

Ile Asp Ile His His Leu Ser Cys Pro Asn Asn Leu Val Val Glu Asp
                20                  25                  30

Glu Gly Cys Thr Asn Leu Ser Glu Phe Ser Tyr Met Glu Leu Lys Val
        35                  40                  45

Gly Tyr Ile Ser Ala Ile Lys Val Asn Gly Phe Thr Cys Thr Gly Val
    50                  55                  60

Val Thr Glu Ala Glu Thr Tyr Thr Asn Phe Val Gly Tyr Val Thr Thr
65                  70                  75                  80

Thr Phe Lys Arg Lys His Phe Arg Pro Thr Pro Asp Ala Cys Arg Ala
                85                  90                  95

Ala Tyr Asn Trp Lys Met Ala Gly Asp Pro Arg Tyr Glu Glu Ser Leu
            100                 105                 110

His Asn Pro Tyr Pro Asp Tyr His Trp Leu Arg Thr Val Arg Thr Thr
        115                 120                 125

Lys Glu Ser Leu Ile Ile Ile Ser Pro Ser Val Thr Asp Leu Asp Pro
130                 135                 140

Tyr Asp Lys Ser Leu His Ser Arg Val Phe Pro Gly Gly Lys Cys Ser
145                 150                 155                 160

Gly Ile Thr Val Ser Ser Thr Tyr Cys Ser Thr Asn His Asp Tyr Thr
                165                 170                 175

Ile Trp Met Pro Glu Asn Pro Arg Pro Arg Thr Pro Cys Asp Ile Phe
            180                 185                 190

Thr Asn Ser Arg Gly Lys Arg Ala Ser Lys Gly Asn Lys Thr Cys Gly
        195                 200                 205

Phe Val Asp Glu Arg Gly Leu Tyr Lys Ser Leu Lys Gly Ala Cys Arg
210                 215                 220

Leu Lys Leu Cys Gly Val Leu Gly Leu Arg Leu Met Asp Gly Thr Trp
225                 230                 235                 240

Val Ala Met Gln Thr Ser Asp Glu Thr Lys Trp Cys Pro Pro Asp Gln
                245                 250                 255

Leu Val Asn Leu His Asp Phe Arg Ser Asp Glu Ile Glu His Leu Val
            260                 265                 270

Val Glu Glu Leu Val Lys Lys Arg Glu Glu Cys Leu Asp Ala Leu Glu
        275                 280                 285

Ser Ile Met Thr Thr Lys Ser Val Ser Phe Arg Arg Leu Ser His Leu
290                 295                 300

Arg Lys Leu Val Pro Gly Phe Gly Lys Ala Tyr Thr Ile Phe Asn Lys
305                 310                 315                 320

Thr Leu Met Glu Ala Asp Ala His Tyr Lys Ser Val Arg Thr Trp Asn
                325                 330                 335

Glu Thr Ile Pro Ser Lys Gly Cys Leu Lys Val Gly Arg Cys His
                340                 345                 350

Pro His Val Asn Gly Val Phe Phe Asn Gly Ile Ile Leu Gly Pro Asp
            355                 360                 365

Gly His Val Leu Ile Pro Glu Met Gln Ser Ser Leu Leu Gln Gln His
        370                 375                 380

Met Glu Leu Leu Lys Ser Ser Val Ile Pro Leu Met His Pro Leu Ala
385                 390                 395                 400

Asp Pro Ser Thr Val Phe Lys Glu Gly Asp Glu Ala Glu Asp Phe Val
                405                 410                 415

Glu Val His Leu Pro Asp Val Tyr Lys Gln Ile Ser Gly Val Asp Leu
            420                 425                 430

Gly Leu Pro Asn Trp Gly Lys Tyr
        435                 440

<210> SEQ ID NO 38
<211> LENGTH: 32
<212> TYPE: PRT
<213> ORGANISM: Homo sapiens

<400> SEQUENCE: 38

Val Ser Arg Leu Glu Glu Met Arg Lys Leu Gln Ala Thr Val Gln
1               5                   10                  15

Glu Leu Gln Lys Arg Leu Asp Arg Leu Glu Glu Thr Val Gln Ala Lys
            20                  25                  30

<210> SEQ ID NO 39
<211> LENGTH: 488
<212> TYPE: PRT
<213> ORGANISM: Artificial Sequence
<220> FEATURE:
<223> OTHER INFORMATION: Synthetic

<400> SEQUENCE: 39

Lys Phe Pro Ile Tyr Thr Ile Pro Asp Lys Leu Gly Pro Trp Ser Pro
1               5                   10                  15

Ile Asp Ile His His Leu Ser Cys Pro Asn Asn Leu Val Val Glu Asp
            20                  25                  30

Glu Gly Cys Thr Asn Leu Ser Glu Phe Ser Tyr Met Glu Leu Lys Val
        35                  40                  45

Gly Tyr Ile Ser Ala Ile Lys Val Asn Gly Phe Thr Cys Thr Gly Val
    50                  55                  60

Val Thr Glu Ala Glu Thr Tyr Thr Asn Phe Val Gly Tyr Val Thr Thr
65                  70                  75                  80

Thr Phe Lys Arg Lys His Phe Arg Pro Thr Pro Asp Ala Cys Arg Ala
                85                  90                  95

Ala Tyr Asn Trp Lys Met Ala Gly Asp Pro Arg Tyr Glu Glu Ser Leu
            100                 105                 110

His Asn Pro Tyr Pro Asp Tyr His Trp Leu Arg Thr Val Arg Thr Thr
        115                 120                 125

Lys Glu Ser Leu Ile Ile Ile Ser Pro Ser Val Thr Asp Leu Asp Pro
    130                 135                 140

Tyr Asp Lys Ser Leu His Ser Arg Val Phe Pro Gly Gly Lys Cys Ser
145                 150                 155                 160

Gly Ile Thr Val Ser Ser Thr Tyr Cys Ser Thr Asn His Asp Tyr Thr
                165                 170                 175

Ile Trp Met Pro Glu Asn Pro Arg Pro Arg Thr Pro Cys Asp Ile Phe

```
              180                 185                 190
Thr Asn Ser Arg Gly Lys Arg Ala Ser Lys Gly Asn Lys Thr Cys Gly
            195                 200                 205
Phe Val Asp Glu Arg Gly Leu Tyr Lys Ser Leu Lys Gly Ala Cys Arg
            210                 215                 220
Leu Lys Leu Cys Gly Val Leu Gly Leu Arg Leu Met Asp Gly Thr Trp
225                 230                 235                 240
Val Ala Met Gln Thr Ser Asp Glu Thr Lys Trp Cys Pro Pro Asp Gln
                245                 250                 255
Leu Val Asn Leu His Asp Phe Arg Ser Asp Glu Ile Glu His Leu Val
                260                 265                 270
Val Glu Glu Leu Val Lys Lys Arg Glu Glu Cys Leu Asp Ala Leu Glu
                275                 280                 285
Ser Ile Met Thr Thr Lys Ser Val Ser Phe Arg Arg Leu Ser His Leu
                290                 295                 300
Arg Lys Leu Val Pro Gly Phe Gly Lys Ala Tyr Thr Ile Phe Asn Lys
305                 310                 315                 320
Thr Leu Met Glu Ala Asp Ala His Tyr Lys Ser Val Arg Thr Trp Asn
                325                 330                 335
Glu Ile Ile Pro Ser Lys Gly Cys Leu Lys Val Gly Arg Cys His
                340                 345                 350
Pro His Val Asn Gly Val Phe Phe Asn Gly Ile Ile Leu Gly Pro Asp
                355                 360                 365
Gly His Val Leu Ile Pro Glu Met Gln Ser Ser Leu Leu Gln Gln His
                370                 375                 380
Met Glu Leu Leu Lys Ser Ser Val Ile Pro Leu Met His Pro Leu Ala
385                 390                 395                 400
Asp Pro Ser Thr Val Phe Lys Glu Gly Asp Ala Glu Asp Phe Val
                405                 410                 415
Glu Val His Leu Pro Asp Val Tyr Lys Gln Ile Ser Gly Val Asp Leu
                420                 425                 430
Gly Leu Pro Asn Trp Gly Lys Tyr Gly Gly Gly Ser Val Ser Arg
                435                 440                 445
Leu Glu Glu Glu Met Arg Lys Leu Gln Ala Thr Val Gln Glu Leu Gln
            450                 455                 460
Lys Arg Leu Asp Arg Leu Glu Glu Thr Val Gln Ala Lys Ala Ser Gly
465                 470                 475                 480
Ala Ala His His His His His His
                485

<210> SEQ ID NO 40
<211> LENGTH: 488
<212> TYPE: PRT
<213> ORGANISM: Artificial Sequence
<220> FEATURE:
<223> OTHER INFORMATION: Synthetic

<400> SEQUENCE: 40

Lys Phe Pro Ile Tyr Thr Ile Pro Asp Lys Leu Gly Pro Trp Ser Pro
1               5                   10                  15
Ile Asp Ile His His Leu Ser Cys Pro Asn Asn Leu Val Val Glu Asp
                20                  25                  30
Glu Gly Cys Thr Asn Leu Ser Glu Phe Ser Tyr Met Glu Leu Lys Val
            35                  40                  45
Gly Tyr Ile Ser Ala Ile Lys Val Asn Gly Phe Thr Cys Thr Gly Val
```

-continued

```
                50                  55                  60
Val Thr Glu Ala Glu Thr Tyr Thr Asn Phe Val Gly Tyr Val Thr Thr
 65                  70                  75                  80

Thr Phe Lys Arg Lys His Phe Arg Pro Thr Pro Asp Ala Cys Arg Ala
                 85                  90                  95

Ala Tyr Asn Trp Lys Met Ala Gly Asp Pro Arg Tyr Glu Glu Ser Leu
                100                 105                 110

His Asn Pro Tyr Pro Asp Tyr His Trp Leu Arg Thr Val Arg Thr Thr
                115                 120                 125

Lys Glu Ser Leu Ile Ile Ile Ser Pro Ser Val Thr Asp Leu Asp Pro
                130                 135                 140

Tyr Asp Lys Ser Leu His Ser Arg Val Phe Pro Gly Gly Lys Cys Ser
145                 150                 155                 160

Gly Ile Thr Val Ser Ser Thr Tyr Cys Ser Thr Asn His Asp Tyr Thr
                165                 170                 175

Ile Trp Met Pro Glu Asn Pro Arg Pro Arg Thr Pro Cys Asp Ile Phe
                180                 185                 190

Thr Asn Ser Arg Gly Lys Arg Ala Ser Lys Gly Asn Lys Thr Cys Gly
                195                 200                 205

Phe Val Asp Glu Arg Gly Leu Tyr Lys Ser Leu Lys Gly Ala Cys Arg
210                 215                 220

Leu Lys Leu Cys Glu Val Leu Gly Leu Arg Leu Met Asp Gly Thr Trp
225                 230                 235                 240

Val Ala Met Gln Thr Ser Asp Glu Thr Lys Trp Cys Pro Pro Asp Gln
                245                 250                 255

Leu Val Asn Leu His Asp Phe Arg Ser Asp Glu Ile Glu His Leu Val
                260                 265                 270

Val Glu Glu Leu Val Lys Lys Arg Glu Glu Cys Leu Asp Ala Leu Glu
                275                 280                 285

Ser Ile Met Thr Thr Lys Ser Val Ser Phe Arg Arg Leu Ser His Leu
                290                 295                 300

Arg Lys Leu Val Pro Gly Phe Gly Lys Ala Tyr Thr Ile Phe Asn Lys
305                 310                 315                 320

Thr Leu Met Glu Ala Asp Ala His Tyr Lys Ser Val Arg Thr Trp Asn
                325                 330                 335

Glu Ile Ile Pro Ser Lys Gly Cys Leu Lys Val Gly Gly Arg Cys His
                340                 345                 350

Pro His Val Asn Gly Val Phe Phe Asn Gly Ile Ile Leu Gly Pro Asp
                355                 360                 365

Gly His Val Leu Ile Pro Glu Met Gln Ser Ser Leu Leu Gln Gln His
                370                 375                 380

Met Glu Leu Leu Lys Ser Ser Val Ile Pro Leu Met His Pro Leu Ala
385                 390                 395                 400

Asp Pro Ser Thr Val Phe Lys Glu Gly Asp Glu Ala Glu Asp Phe Val
                405                 410                 415

Glu Val His Leu Pro Asp Val Tyr Lys Gln Ile Ser Gly Val Asp Leu
                420                 425                 430

Gly Leu Pro Asn Trp Gly Lys Tyr Gly Gly Gly Ser Val Ser Arg
                435                 440                 445

Leu Glu Glu Glu Met Arg Lys Leu Gln Ala Thr Val Gln Glu Leu Gln
                450                 455                 460

Lys Arg Leu Asp Arg Leu Glu Glu Thr Val Gln Ala Lys Ala Ser Gly
465                 470                 475                 480
```

Ala Ala His His His His His His
                485

<210> SEQ ID NO 41
<211> LENGTH: 488
<212> TYPE: PRT
<213> ORGANISM: Artificial Sequence
<220> FEATURE:
<223> OTHER INFORMATION: Synthetic

<400> SEQUENCE: 41

Lys Phe Pro Ile Tyr Thr Ile Pro Asp Lys Leu Gly Pro Trp Ser Pro
1               5                   10                  15

Ile Asp Ile His His Leu Ser Cys Pro Asn Asn Leu Val Val Glu Asp
            20                  25                  30

Glu Gly Cys Thr Asn Leu Ser Glu Phe Ser Tyr Met Glu Leu Lys Val
        35                  40                  45

Gly Tyr Ile Ser Ala Ile Lys Val Asn Gly Phe Thr Cys Thr Gly Val
    50                  55                  60

Val Thr Glu Ala Glu Thr Tyr Thr Asn Phe Val Gly Tyr Val Thr Thr
65                  70                  75                  80

Thr Phe Lys Arg Lys His Phe Arg Pro Thr Pro Asp Ala Cys Arg Ala
                85                  90                  95

Ala Tyr Asn Trp Lys Met Ala Gly Asp Pro Arg Tyr Glu Glu Ser Leu
            100                 105                 110

His Asn Pro Tyr Pro Asp Tyr His Trp Leu Arg Thr Val Arg Thr Thr
        115                 120                 125

Lys Glu Ser Leu Ile Ile Ile Ser Pro Ser Val Thr Asp Leu Asp Pro
    130                 135                 140

Tyr Asp Lys Ser Leu His Ser Arg Val Phe Pro Gly Gly Lys Cys Ser
145                 150                 155                 160

Gly Ile Thr Val Ser Ser Thr Tyr Cys Ser Thr Asn His Asp Tyr Thr
                165                 170                 175

Ile Trp Met Pro Glu Asn Pro Arg Pro Arg Thr Pro Cys Asp Ile Phe
            180                 185                 190

Thr Asn Ser Arg Gly Lys Arg Ala Ser Lys Gly Asn Lys Thr Cys Gly
        195                 200                 205

Phe Val Asp Glu Arg Gly Leu Tyr Lys Ser Leu Lys Gly Ala Cys Arg
    210                 215                 220

Leu Lys Leu Cys Gly Val Leu Gly Leu Arg Leu Met Asp Gly Thr Trp
225                 230                 235                 240

Val Ala Met Gln Thr Ser Asp Glu Thr Lys Trp Cys Pro Pro Asp Gln
                245                 250                 255

Leu Val Asn Leu His Asp Phe Arg Ser Asp Glu Ile Glu His Leu Val
            260                 265                 270

Val Glu Glu Leu Val Lys Lys Arg Glu Glu Cys Leu Asp Ala Leu Glu
        275                 280                 285

Ser Ile Met Thr Thr Lys Ser Val Ser Phe Arg Arg Leu Ser His Leu
    290                 295                 300

Arg Lys Leu Val Pro Gly Phe Gly Lys Ala Tyr Thr Ile Phe Asn Lys
305                 310                 315                 320

Thr Leu Met Glu Ala Asp Ala His Tyr Lys Ser Val Arg Thr Trp Asn
                325                 330                 335

Glu Thr Ile Pro Ser Lys Gly Cys Leu Lys Val Gly Gly Arg Cys His
            340                 345                 350

```
Pro His Val Asn Gly Val Phe Phe Asn Gly Ile Ile Leu Gly Pro Asp
        355                 360                 365
Gly His Val Leu Ile Pro Glu Met Gln Ser Ser Leu Leu Gln Gln His
    370                 375                 380
Met Glu Leu Leu Lys Ser Ser Val Ile Pro Leu Met His Pro Leu Ala
385                 390                 395                 400
Asp Pro Ser Thr Val Phe Lys Glu Gly Asp Glu Ala Glu Asp Phe Val
                405                 410                 415
Glu Val His Leu Pro Asp Val Tyr Lys Gln Ile Ser Gly Val Asp Leu
            420                 425                 430
Gly Leu Pro Asn Trp Gly Lys Tyr Gly Gly Gly Ser Val Ser Arg
        435                 440                 445
Leu Glu Glu Glu Met Arg Lys Leu Gln Ala Thr Val Gln Glu Leu Gln
    450                 455                 460
Lys Arg Leu Asp Arg Leu Glu Glu Thr Val Gln Ala Lys Ala Ser Gly
465                 470                 475                 480
Ala Ala His His His His His His
            485
```

```
<210> SEQ ID NO 42
<211> LENGTH: 5
<212> TYPE: PRT
<213> ORGANISM: Artificial Sequence
<220> FEATURE:
<223> OTHER INFORMATION: Synthetic

<400> SEQUENCE: 42

Arg Tyr Thr Ile Asn
1               5

<210> SEQ ID NO 43
<211> LENGTH: 17
<212> TYPE: PRT
<213> ORGANISM: Artificial Sequence
<220> FEATURE:
<223> OTHER INFORMATION: Synthetic

<400> SEQUENCE: 43

Gly Ile Ile Pro Ile Phe Gly Thr Ala Asn Tyr Ala Gln Arg Phe Gln
1               5                   10                  15
Gly

<210> SEQ ID NO 44
<211> LENGTH: 19
<212> TYPE: PRT
<213> ORGANISM: Artificial Sequence
<220> FEATURE:
<223> OTHER INFORMATION: Synthetic

<400> SEQUENCE: 44

Glu Asn Leu Asp Asn Ser Gly Thr Tyr Tyr Tyr Phe Ser Gly Trp
1               5                   10                  15

Phe Asp Pro

<210> SEQ ID NO 45
<211> LENGTH: 14
<212> TYPE: PRT
<213> ORGANISM: Artificial Sequence
<220> FEATURE:
<223> OTHER INFORMATION: Synthetic
```

```
<400> SEQUENCE: 45

Thr Gly Thr Ser Ser Asp Ile Gly Ala Tyr Asp Tyr Val Ser
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Synthetic

<400> SEQUENCE: 46

Asp Ala Thr Lys Arg Pro Ser
1               5

<210> SEQ ID NO 47
<211> LENGTH: 12
<212> TYPE: PRT
<213> ORGANISM: Artificial Sequence
<220> FEATURE:
<223> OTHER INFORMATION: Synthetic

<400> SEQUENCE: 47

Cys Ser Tyr Ala Gly Asp Tyr Thr Pro Gly Val Val
1               5                   10

<210> SEQ ID NO 48
<211> LENGTH: 5
<212> TYPE: PRT
<213> ORGANISM: Artificial Sequence
<220> FEATURE:
<223> OTHER INFORMATION: Synthetic

<400> SEQUENCE: 48

Arg Tyr Ser Ile Asn
1               5

<210> SEQ ID NO 49
<211> LENGTH: 14
<212> TYPE: PRT
<213> ORGANISM: Artificial Sequence
<220> FEATURE:
<223> OTHER INFORMATION: Synthetic

<400> SEQUENCE: 49

Thr Gly Thr Ser Ser Asp Ile Asp Gly Tyr Asp Phe Val Ser
1               5                   10

<210> SEQ ID NO 50
<211> LENGTH: 5
<212> TYPE: PRT
<213> ORGANISM: Artificial Sequence
<220> FEATURE:
<223> OTHER INFORMATION: Synthetic

<400> SEQUENCE: 50

Gly Tyr Thr Ile Asn
1               5

<210> SEQ ID NO 51
<211> LENGTH: 14
<212> TYPE: PRT
<213> ORGANISM: Artificial Sequence
<220> FEATURE:
<223> OTHER INFORMATION: Synthetic

<400> SEQUENCE: 51
```

```
Thr Gly Thr Ser Ser Asp Leu Gly Gly Tyr Asp Phe Val Ser
1               5                   10

<210> SEQ ID NO 52
<211> LENGTH: 5
<212> TYPE: PRT
<213> ORGANISM: Artificial Sequence
<220> FEATURE:
<223> OTHER INFORMATION: Synthetic

<400> SEQUENCE: 52

Ser Tyr Gly Met His
1               5

<210> SEQ ID NO 53
<211> LENGTH: 17
<212> TYPE: PRT
<213> ORGANISM: Artificial Sequence
<220> FEATURE:
<223> OTHER INFORMATION: Synthetic

<400> SEQUENCE: 53

Thr Ile Ser Tyr Asp Gly Ser Ile Lys Asp Tyr Ala Asp Ser Val Lys
1               5                   10                  15

Gly

<210> SEQ ID NO 54
<211> LENGTH: 9
<212> TYPE: PRT
<213> ORGANISM: Artificial Sequence
<220> FEATURE:
<223> OTHER INFORMATION: Synthetic

<400> SEQUENCE: 54

Gly Asp Arg Thr Gly Asn Leu Asp Tyr
1               5

<210> SEQ ID NO 55
<211> LENGTH: 11
<212> TYPE: PRT
<213> ORGANISM: Artificial Sequence
<220> FEATURE:
<223> OTHER INFORMATION: Synthetic

<400> SEQUENCE: 55

Arg Ala Ser Gln Asn Ile Arg Asn Ala Leu Asn
1               5                   10

<210> SEQ ID NO 56
<211> LENGTH: 7
<212> TYPE: PRT
<213> ORGANISM: Artificial Sequence
<220> FEATURE:
<223> OTHER INFORMATION: Synthetic

<400> SEQUENCE: 56

Asp Ala Ser Thr Arg Gln Ser
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic
```

<400> SEQUENCE: 57

Gln Gln Asn Ser Glu Phe Pro Pro Thr
1               5

<210> SEQ ID NO 58
<211> LENGTH: 16
<212> TYPE: PRT
<213> ORGANISM: Artificial Sequence
<220> FEATURE:
<223> OTHER INFORMATION: Synthetic

<400> SEQUENCE: 58

Gly Gly Gly Gly Gly Ser Gly Gly Gly Gly Ser Gly Gly Gly Gly Ser
1               5                   10                  15

<210> SEQ ID NO 59
<211> LENGTH: 28
<212> TYPE: DNA
<213> ORGANISM: Artificial Sequence
<220> FEATURE:
<223> OTHER INFORMATION: Synthetic

<400> SEQUENCE: 59
ccagccatgg cgcaggtgca gctggtgc                                              28

<210> SEQ ID NO 60
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (25)..(25)
<223> OTHER INFORMATION: n can be any deoxynucleotide

<400> SEQUENCE: 60
ctggggcctg ccgcacccag yyganasyaw atbygyyawa ggtgccgccg ctggccttgc            60

<210> SEQ ID NO 61
<211> LENGTH: 19
<212> TYPE: DNA
<213> ORGANISM: Artificial Sequence
<220> FEATURE:
<223> OTHER INFORMATION: Synthetic

<400> SEQUENCE: 61
tgggtgcggc aggccccag                                                        19

<210> SEQ ID NO 62
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (38)..(38)
<223> OTHER INFORMATION: n can be any deoxynucleotide

<400> SEQUENCE: 62
tgctgctgat accagctcac awagyyawaa bcabcgangt cgctgctggt gccg                 54

<210> SEQ ID NO 63
<211> LENGTH: 20
<212> TYPE: DNA
<213> ORGANISM: Artificial Sequence

```
<220> FEATURE:
<223> OTHER INFORMATION: Synthetic

<400> SEQUENCE: 63
gtgagctggt atcagcagca                                                   20

<210> SEQ ID NO 64
<211> LENGTH: 32
<212> TYPE: DNA
<213> ORGANISM: Artificial Sequence
<220> FEATURE:
<223> OTHER INFORMATION: Synthetic

<400> SEQUENCE: 64
gatgtgcggc cgccaggacg gtaagcttgg tg                                     32
```